(12) United States Patent
Knoll

(10) Patent No.: US 6,548,311 B1
(45) Date of Patent: Apr. 15, 2003

(54) DEVICE AND METHOD FOR DETECTING ANALYTES

(76) Inventor: Meinhard Knoll, Geschwister-Scholl-Strasse 9, D-48565 Steinfurt (DE)

( * ) Notice: Subject to any disclaimer, the term of this patent is extended or adjusted under 35 U.S.C. 154(b) by 0 days.

(21) Appl. No.: 09/554,845
(22) PCT Filed: Nov. 20, 1998
(86) PCT No.: PCT/EP98/07494
§ 371 (c)(1), (2), (4) Date: Jun. 15, 2000
(87) PCT Pub. No.: WO99/27367
PCT Pub. Date: Jun. 3, 1999

(30) Foreign Application Priority Data

Nov. 21, 1997 (DE) .......................................... 197 51 706
May 8, 1998 (DE) .......................................... 198 22 123

(51) Int. Cl.⁷ ........................................... G01N 33/551
(52) U.S. Cl. ..................... 436/524; 436/518; 436/526; 436/525; 422/82.01; 422/98; 422/186.01; 422/186.04; 422/58; 204/403; 435/7.1; 435/285.2
(58) Field of Search .................. 422/82.01, 82.02, 422/82.03, 98, 101, 186.01, 186.03, 186.04, 186.13, 58; 204/450, 516, 518, 400, 403, 411, 415; 435/7.1, 285.2; 436/518, 524, 525

(56) References Cited

U.S. PATENT DOCUMENTS

| | | | | |
|---|---|---|---|---|
| 4,935,207 A | * | 6/1990 | Stanbro et al. | 422/68.1 |
| 5,846,837 A | * | 12/1998 | Thym et al. | 436/170 |
| 5,863,400 A | * | 1/1999 | Drummond et al. | 204/415 |
| 5,916,156 A | * | 6/1999 | Hildenbrand et al. | 600/347 |
| 5,958,791 A | * | 9/1999 | Roberts et al. | 436/514 |
| 6,133,046 A | * | 10/2000 | Clerc et al. | 436/501 |
| 6,284,113 B1 | * | 9/2001 | Bjornson et al. | 204/453 |

FOREIGN PATENT DOCUMENTS

| | | |
|---|---|---|
| EP | 0 402 917 A2 | 12/1990 |
| EP | 0 495 519 A2 | 7/1992 |
| EP | 0 745 843 A2 | 12/1996 |
| WO | WO 87 03095 A1 | 5/1987 |
| WO | WO 88 09808 A2 | 12/1988 |
| WO | WO 90 05300 A1 | 5/1990 |
| WO | WO 97 45740 A1 | 12/1997 |

OTHER PUBLICATIONS

Christopher P. Price and David J. Newman; *Principles and Practice of Immunoassay*; 1991; pp. 96–153; Macmillan Publishers Ltd., U.K.

(List continued on next page.)

*Primary Examiner*—Long V. Le
*Assistant Examiner*—Gary Counts
(74) *Attorney, Agent, or Firm*—Marshall & Melhorn, LLC

(57) ABSTRACT

The invention relates to a method for detecting analytes and to a device for carrying out the method, for use for analysis or diagnosis in the fields of chemistry, biochemistry, molecular genetics, food chemistry, biotechnology, the environment and medicine. Marker particles (5) with different electrical properties or a different relative permeability to those of the measuring solution (3) surrounding them are used to detect the analytes (8). The marker particles (5) either bond specifically to the analytes (8) or to a base (2) in competition with the analyte. The analytes (8) are detected by the changes in an electrical field or an electrical current generated by electrodes (2) or in an electrical voltage applied to an electrode or in a magnetic field, said changes being caused by marker particles which have bonded with the analytes or by marker particles which have instead bonded to the base in an electrical field.

20 Claims, 35 Drawing Sheets

OTHER PUBLICATIONS

Jacques M. Singer, M.D. and Charles M. Plotz, M.D.; "The Latex Fixation Test"; *The American Journal of Medicine*, Dec. 1956; pp. 888–892; New York, New York.

"To affinity . . . and beyond!"; Editorial, *nature genetics*, Dec. 1996; pp. 367–370; vol. 14, No. 4.

Joseph G. Hacia et al.; Detection of heterozygous mutations in BRCA1 using high density oligonucleotide arrays and two–colour. Fluorescence analysis; *nature genetics*, Dec. 1996; pp. 441–447; vol. 14, No. 4.

Daniel D. Shoemaker et al.; "Quantitative phenotypic analysis of yeast deletion mutants using a highly parallel molecular bar–coding strategy"; *nature genetics*, Dec. 1996; pp. 450–456; vol. 14, No. 4.

Deborah Noble; "DNA Sequencing on a Chip"; *Analytical Chemistry*, Mar. 1, 1995; pp. 201A–204A; vol. 67, No. 5.

* cited by examiner

DEVICE AND METHOD FOR DETECTING ANALYTES

BACKGROUND OF THE INVENTION

1. Field of the Invention

The invention relates to a process for detection of analytes and a device for carrying out the process.

Such devices and processes, which are also designated below with the term of assay describing both, serve for qualitative and quantitative recording of specific bonds between at least two molecules. This includes, for example the recording of receptor-ligand interactions, antibody-antigen interaction, recognition of nucleic acids, interaction between oligonucleotides and DNA as well as other molecular interactions. Processes and devices of this type can be used, for example in chemistry, clinical analysis, pharmaceutical development, environmental analysis and in routine molecular biology work including sequencing of nucleic acids.

It is known that immunoassays having different detection methods are carried out. This includes radioactive, fluorescence-assisted and chemoluminescence-assisted and enzymatic processes (C. P. Prince, D. J. Newman: Principles and Practice of Immunoassays, Macmillan Publishers Ltd., 1991 U.K.).

In a particular form of immunoassay there is an agglutination of latex particles due to antibody-antigen bonds, which may be detected, for example visually (J. M. Singer, C. M. Plotz: The Latex Fixation Test, American Journal of Medicine, December 1965, pp. 888–892). $10^5$ molecules may be detected using microspheres of 10 μm diameter, $10^8$ molecules using microspheres having a diameter of 1 μm, and $10^{13}$ molecules using microspheres having a diameter of 0.1 μm with such agglutination tests. Using the example of IgG (MW=100,000) theoretical sensitivities of 10 fM, 10 pM or 10 nM are given. The highest sensitivity is thus seen for relatively large microspheres, the use of which is however limited by their sedimentation behaviour, Furthermore, recently nucleic acids, for example oligonucleotides, RNA and DNA may be detected via such interactions by means of DNA microchip technology (Nature, Genetics, Volume 14, No 4, December 96, and D. Noble: DNA Sequencing on a chip, Anal Chemistry, Volume 67, No. 5. Mar. 1, 1995). However, the chip technology is not used here as an electrical measuring process, but it serves as a novel synthesis process and for producing microstructures. The actual detection mechanism is of visual type. The combination of electrical processes for synthesis of a ligand and the visual marking and detection is however very expensive.

The disadvantage of the state of the art is that detection processes based on radioactivity are burdened with problems of radiation protection and disposal of the radioactive waste thus produced. In enzymatic detection methods which facilitate electrochemical detection of the analytes, a chemical reaction with a substance as the chemical reaction substrate must take place as an additional working step.

In all detection processes and assays known in the state of the art, a final washing step is necessary to remove excess reactants before detection of the analyte to minimise non-specific signals as far as possible.

The object of the invention is to provide a device and a process which facilitates detection of analytes in rapid, simple and precise manner and in which a washing step may be omitted.

2. Description of the Related Art

World application 9005300 relates to a process for detection of binding reaction between specific substances, in which electrodes, between which a gap exists, are applied to a support. A layer of, for example antigens, is applied to the support in the gap. A measuring solution containing marker particles with antibodies and antigens is passed over the support, wherein marker particles with antibodies bind to the antigen layer of the support. After a preset reaction time, the non-bound marker particles are removed by washing and after drying the resistance is measured between the two electrodes which is a measure for binding which has taken place. Depending on the design of the support (conducting or non-conducting), a signal is measured when the gap is not completely bridged by conductive particles or only when the gap is filled.

European application 0 745 843 discloses an electrochemical biosensor which has electrodes and a matrix with different reagents. The reagents include conjugates of analytes and cytolytic reagent, receptors and liposomes containing electroactive materials. The liposomes release the electroactive material under the action of the analyte.

In a biosensor disclosed in European application 0 402 917, an electrically conducting polymer layer, to which a binding partner is coupled, is arranged between the electrodes. When binding the particular binding partner, the electrical properties of the polymer layer are changed.

European application 0 495 519 describes a process for measuring a specific substance in a sample, wherein an alternating current is applied to electrodes shaped like ridges to accelerate the aggregration of charged particles. Aggregation is then measured visually.

This object is achieved according to the invention by the features of the main and sub-claim.

If marker particles having electrical and/or electrochemical properties, which differ from those of their surroundings, the measuring solution, are introduced into an electric field, the electric field is disturbed by this. These disturbances of an electric field produced in the measuring solution may be determined simply, rapidly and very precisely.

SUMMARY OF THE INVENTION

The process of the invention is thus based on a detection method which may be regarded as essentially purely electrical. Therefore it has the very high sensitivity or precision possible for the determination of electrical or electrochemical properties and consequently a very low detection limit at high sensitivity.

With suitable dimensions and/or positioning of the electrodes which produce the electric field, the electric field is virtually exclusively influenced by marker particles having different material composition, different specific resistance of electric surface charge or different dielectric constant, which have undergone specific binding, for example with the analyte or with a substrate, that is bodies or materials suitable as substrate. Excess non-bound marker particles do not lead to a signal, so that a washing step for removing non-bound marker particles from the measuring solution may be omitted.

The measuring range of the bioassay according to the invention (process and/or device) may be adjusted by fixing the electrode or substrate surfaces and by selecting the size of the marker particles.

The process of the invention and the device of the invention may be used for detection and for concentration determination of any analytes which can be recorded via molecular interactions. These include, for example the interactions of receptor-ligand, antibody-antigen, antibody-hapten, antibody fragment-antigen, aptamers, proteins, nucleic acids, oligonucleotides, DNA and all molecular interactions, in which at least one of the molecular partners may be marked with a marker particle. This includes the interaction of materials with the surfaces of whole cells. It is possible in principle to realise all known immunoassay formats according to the state of the art.

The advantages achieved using the invention consequently exist particularly in the fact that a purely electrical detection method is used having all its advantages with reference to precision, rapidity and sensitivity, and that also when using very small electrodes and marker particles of comparable size, individual bond detection is possible.

Advantageous further developments of the process of the invention and the device of the invention are given in the dependent claims.

Particularly in the near-field of an electrode producing an electric field, even the presence of a single marker particle may lead to adequately high changes in the electric field. Non-specifically bound marker particles further removed from the electrode lead to fewer impairments of the electric field, so that with suitable arrangement of the electrodes in the vicinity of a substrate or design of the electrodes themselves as a substrate and at suitable concentration of the marker particles, the measured signal is influenced essentially only by specifically bound marker particles. Hence, a washing step for removing excess marker particles or analytes from the measuring solution may then also be omitted.

When using marker particles, the relative permeability of which differs from the relative permeability of the measuring solution, wherein a magnetic field is produced at or in the measuring solution, detection may be provided by the strength of the magnetic field or by its change caused by the marker particles.

Hence, for example individual bond detection may take place at an electrode as substrate, the surface of which lies in the same order of magnitude as the largest cross-sectional surface area of the marker particle or at least does not differ by several orders of magnitude. Hence microelectrodes may be used for this, which have round, square, rectangular, but also any shape. The diameters of the marker particles lie between a few nm to a few $\mu$m, for example 10 $\mu$m.

If binding of several marker particles is to be detected by measuring technology, larger electrodes may be used, at the surface of which there is surface covering including three-dimensional agglutination of marker particles. In contrast to the values given for the state of the art for agglutination tests, the theoretical detection limit drops as a function of the diameter of the marker particles by several orders of magnitude.

Furthermore, the measuring range of the bioassay may be adjusted by fixing the electrode surfaces between the individual bond region and the agglutination region.

When using only one microelectrode or very few microelectrodes (with an associated counter-electrode), very low analyte concentrations may be recorded when the measuring medium surrounding the microelectrode(s) has just a small volume with a limited number of marker particles. Simpler, more precise individual bond detection may therefore be realised by using a very small sample chamber or through-flow chamber in the order of magnitude of $\mu$l.

This applies particularly in the detection of analytes by their specific binding to marker particles in a through-flow measuring system, wherein here the analyte stream takes with it the bound marker particles by means of an electric field applied externally via electrodes. The changes in electric field which are shown as changes in the electric current or capacity between the electrodes in the measuring solution and which are triggered by the marker particles, may be recorded precisely. Individual detection is also possible here with a corresponding low volume of the through-flow region.

If an electric or magnetic field alternating its polarity is applied to the measuring solution, improved mixing of the analytes and the marker particles may be achieved by the movement thus caused of electrically charged or magnetic (paramagnetic or diamagnetic) marker particles. Paramagnetic marker particles are particularly suitable for this, since a considerably lower magnetic field is required than for diamagnetic marker particles. The precision and reproducibility of any marker-assisted detection process may be improved by such field-induced mixing. The marker particles having immobilised molecules may thus also include those which do not carry any molecules. These additional marker particles increase the mixing effect. This mixing of the measuring medium may additionally be supported by connecting ultrasound.

Furthermore, such marker particles may be moved to their binding sites on the substrate by corresponding electric or magnetic fields due to electrophoretic or magnetically induced transport, or may be removed from the vicinity of the substrate after binding of excess marker particles is completed. The markers present in the measuring solution are better utilised due to this electrophoretic or magnetic field-induced transport of the marker particles to their binding sites, and the sensitivity, the detection limit and the reproducibility as well as the precision of the processes of the invention is greatly improved. Due to the electrophoretic or magnetic field-induced transport of the residual non-bound marker particles, taking place on the bond of the marker particles at their binding sites, away from the binding sites, their concentration is greatly reduced in the region of the substrate and/or the electrodes. As a result of the sensitivity of the electrodes to disturbances, particularly in their near-field, the free marker particles still influence the measurement only insignificantly. A special washing step, which is necessary according to the state of the art for many analytical processes, in particular immunoassays, may also therefore be omitted.

If the molecules to be detected in the measuring process and the molecule-charged marker particles have electric charges of different polarity, when applying an electric voltage, electrophoretic transport initially transports the charged molecules to their binding sites on or in the surroundings of the electrodes. After binding to the binding sites is completed, by reversing the polarity of the electric field, the molecule-charged marker particles are brought to the binding sites on or in the vicinity of the electrodes. This process is particularly advantageous when using sandwich format assays.

The described direct transport of electrically charged or magnetic particles induced by an electric or magnetic field and alternating transport orientated to mixing, can be used for all marker-assisted detection processes proceeding in measuring solutions.

When using inhomogeneous electric fields, uncharged, but polar marker particles may also be transported directed by the process given above or mixed.

In accordance with an exemplary embodiment of the invention, an electrode is used in front of which a diaphragm having at least one small opening is arranged. The diaphragm thus faces the measuring solution and via the electrode an inhomogeneous electric field is produced, the field lines of which pass through the small opening in the diaphragm. The marker particles are bound to or in the vicinity of the surface of the diaphragm. The advantages achieved using this embodiment consist particularly in that to produce an inhomogeneous electric field, a microelectrode having a diameter in the μm range and smaller does not have to be produced, since the diaphragm opening is important for the electric field. The production of microelectrodes is indeed known, but it requires an expensive technological process with high costs. When using a diaphragm in front of a macroelectrode, the technological requirements in electrode production are not so high, so that the device of the invention can be produced with low costs. Hence, measuring devices with individual electrodes or electrode arrays may be produced as disposable articles with low costs.

A further advantage of the invention consists in that the current which flows through the small diaphragm opening to the counter-electrode in the measuring solution, only causes a very small current density at the electrode. Compared to using a microelectrode, in this case the current density is smaller by the ratio of the cross-sectional surface area of the diaphragm opening and electrode surface. This results in changes in the electrical resistance being caused mainly by particle-induced field disturbances and the influence of electrochemical electrode reactions is largely negligible. The measurements may be carried out more precisely in this manner.

In accordance with a further exemplary embodiment of the present invention, the measurement of detection of the disturbances to the electric field caused by the marker particles is carried out in the measuring solution using a potentiometric process, wherein the electric field is formed at the surface of an electrode by potential-forming steps at the boundary between measuring solution and electrode.

The advantages of this embodiment consist particularly in that likewise electrodes having greater diameter or greater surface may be used. This can be seen from the fact that the potential-forming steps on the surface of a potentiometric electrode occur at distances from this electrode which lie in the same order of magnitude as the diameter of marker particles. Marker particles in the nm range to the μm range may be used in this manner.

It is important for application in a potentiometric measuring process that the marker particles have a significantly different electric charge and/or potential difference in the liquid measuring medium at their surface than the ion-selective electrode itself. This is a favourable premise in potentiometric detection for binding of marker particles.

It is additionally possible both for the amperometric and for the potentiometric detection process to influence the potential ratios at the surface of the marker particles in that the marker particles are doped with ionophores, as is also the case for ion-selective membranes. Other ionophores should thus be used than in the ion-selective membrane which serves for detection of the bound marker particles. Likewise, it is possible to provide marker particles with a thin metal layer on the surface.

Both in the amperometric and in the potentiometric detection process, detection of analytes may be effected in a two-step process which comprises marker particle transport and then binding to the electrode, As described, electrophoretic and magnetic marker particle transport may be used here.

Exemplary embodiments of the invention are shown in the drawing and are illustrated in more detail in the description below.

DESCRIPTION OF THE EMBODIMENTS

Figure 1:
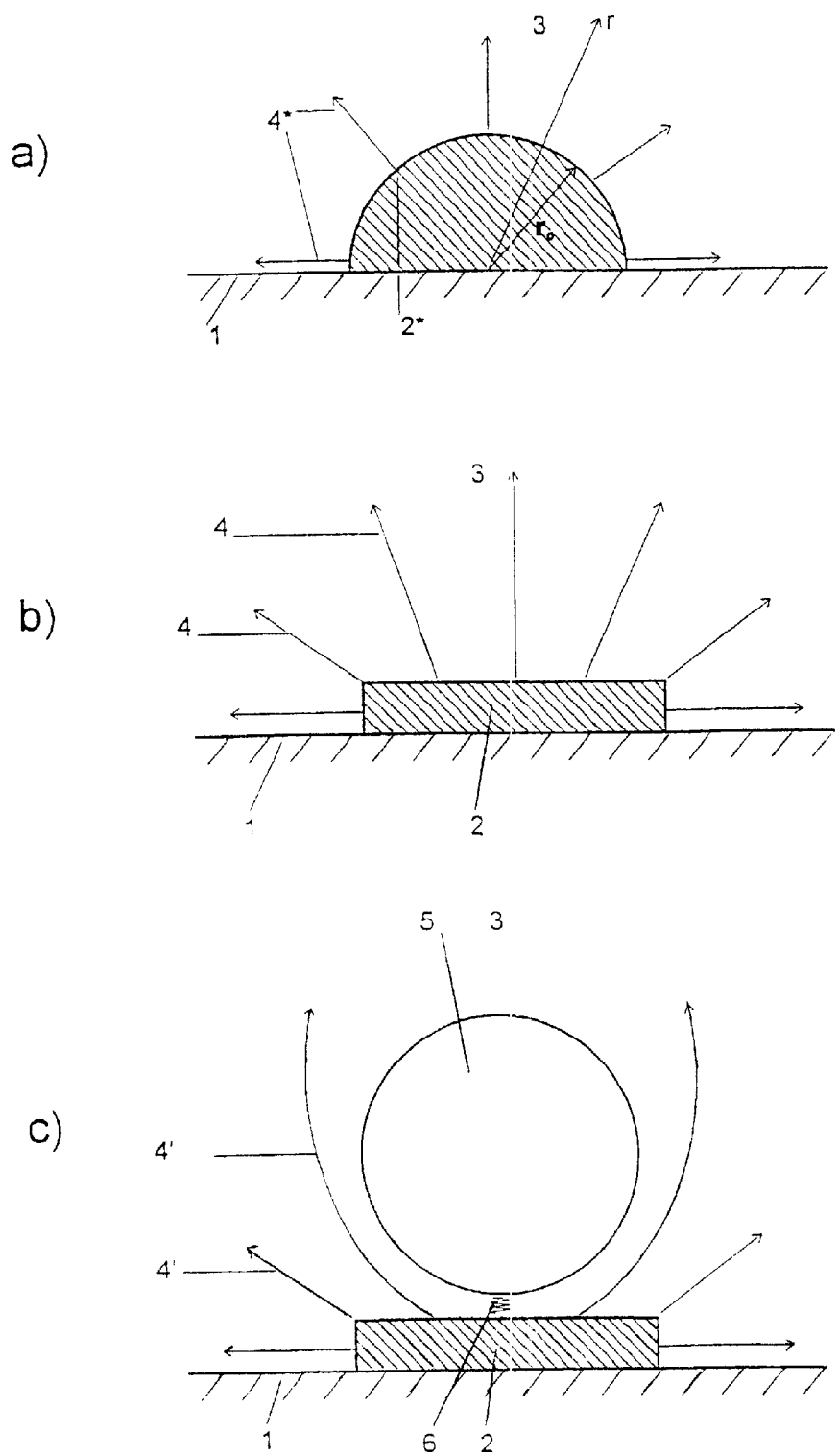
FIG. 1 shows the electric flow field in the surroundings of a microelectrode
   *a*) spherical microelectrode
   *b*) planar microelectrode
   *c*) planar microelectrode with marker particles in the flow field FIG. 2 Electrophoretic marker particle transport
   *a*+*b*) to the microelectrode or
   *c*) away from the microelectrode FIG. 3 Macroelectrode with agglutinated marker particles FIG. 4 Through-flow cell with two microelectrodes,
   *a*) without marker particles
   *b*) with one marker particle and
   *c*) with two bound marker particles FIG. 5 Immunoassay formats
   *a*) and *b*) antigen detection
   *c*) and *d*) antibody detection
   *a*) and *c*) sandwich process and
   *b*) and *d*) competitive processes FIG. 6 Immunoassay according to FIG. 5*a*) with additional membrane FIG. 7 Immunoassay formats in the through-flow process
   *a*) and *b*) antigen detection
   *c*) and *d*) antibody detection
   *a*) and *c*) sandwich process
   *b*) and *d*) competitive processes FIGS. 8*a*–*e* DNA probe with antibody interaction FIGS. 9*a*–*c* DNA probe FIGS. 10*a*–*d* DNA probe according to the sandwich principle FIGS. 11*a*–*c* Immunoassay array FIGS. 12*a*–*b* Cross-section through an immunoassay array FIGS. 13*a*–*b* Micro-containment assay FIGS. 14*a*–*b* Bioassay based on interdigital structures FIGS. 15*a*–*b* Modified assay according to FIG. 14

The mechanism of binding detection is described in more detail in FIG. 1.

FIG. 1a) shows the surroundings of a microelectrode. Here 1 is an insulating support, on which a spherical microelectrode 2* is arranged. An electric voltage is applied between this microelectrode 2* and a counter-electrode not shown. Both electrodes are surrounded by a liquid measuring medium 3. Electrical field lines 4 emerge from the live microelectrode 2*. FIGS. 1b) and 1c) show the mechanism of binding detection. The planar microelectrode 2 has square shape having an edge length of 3 μm. The electrode has been produced with the aid of known thin-layer processes on an insulating support 1 which consists of glass. The material of the marker particle is, for example $SiO_2$, and the diameter is 2 μm.

In aqueous measuring medium, the specific conductivity is described as follows:

$$\kappa = \sum_i Z_i^1 \cdot F^2 \cdot \mu_i \cdot C_1 \qquad \text{Equation 1}$$

Herein $z_i$ is the charge number, $\mu$ is the mobility and C the concentration of the ions. F represents the Faraday constant.

The relationships between electrical current density, electrical field strength and voltage drop between microelectrode and liquid measuring medium are simplified as follows:

A relationship between the current density J and the electric current I can be seen on a hemispherical microelectrode according to equation 2.

$$J = \frac{1}{2\pi r^2} \qquad \text{Equation 2}$$

Herein r is the distance from the central point of the microelectrode into the measuring medium. The equation $$E = \frac{1}{\kappa} \cdot J \qquad \text{Equation 3}$$

applies for the electric field strength E with the specific conductivity K of the measuring medium.

For the voltage drop between the electrode surface and the liquid measuring medium the result as a function of the radius r is $$U_g = \int_{r_o}^{r} E \, dr = \frac{1}{2\pi\kappa}\left(\frac{1}{r_o} - \frac{1}{r}\right) \qquad \text{Equation 4}$$

For a planar microelectrode according to FIG. 1b) it follows:

$$U_s' = U_s \cdot k \text{ with } k \approx 0.6 \qquad \text{Equation 5}$$

For the distance $r = 2r_o$ it follows $$U_s(r=2r_o) = 0.5 U(r \to \infty) \qquad \text{Equation 6}$$

This means that even at a distance from an electrode diameter the voltage has dropped by 50%.

A disturbance in the electric field in the immediate surroundings of the microelectrode 2* thus leads to a strong change in the electric field line path.

FIG. 1c) shows a marker particle (label particle) 5 which is bound via a bond 6 to a microelectrode 2 as substrate. The electric flow field 4 strongly disturbed by the marker particle 5 has the effect of a strong change in the measurable electrical resistance between the microelectrode 2 and a counter-electrode, which is likewise situated in the aqueous measuring medium 3, but is not shown.

The electrical resistance may be measured with the aid of direct or alternating voltages with values of a few 10 mV to a few volts, preferably in the 100 mV range, and the electrical capacity may be measured with the aid of alternating voltages with frequencies of a few Hz to a few MHz, preferably in the kHz range.

If binding of marker particles 5 is recorded in time-resolved manner in the space near the electrode by measuring the electrical resistance or the electrical capacity, quantitative measurement may take place by dynamic means by evaluating the signal-time function, since its first derivation is a measure of the analyte concentration.

The molecular interaction of the marker particles 5 with the substrate is further assisted by transport of marker particles 5 in an electric field, provided the marker particles 5 themselves are electrically charged. This may be described as follows.

In the electric field E, which is produced between two electrodes by applying an electric voltage in the aqueous measuring medium, a force F is exerted on an electrically charged marker particle 5:

$$F = z_i \cdot Q \cdot E \qquad \text{Equation 7}$$

Herein Q is the charge of the ions.

The electrically charged marker particles 5 having a speed v in the electric field E are moved due to this force effect:

$$v = \mu \cdot E \qquad \text{Equation 9}$$

The speed of the marker particle (v) is thus proportional to the electric field strength E. This proportionality is described by the mobility $\mu$:

$$\mu = V/E \qquad \text{Equation 10}$$

The mobility $\mu$ is thus dependent on the type of measuring medium and the type of marker particles.

This means that the marker particles move in the electric field due to their own electric charge. Furthermore, if electrically charged molecules are situated on the surface of the marker particles, the separate charge of the marker particle in any case determines the direction of field-induced transport, if the extent of the separate charge is greater than the extent of the charges of the molecules bound to the surface. If the charge of the bound molecules has the same polarity as the marker particles own charge, the transport is promoted by increasing the speed. The speed is reduced for opposing charges.

Figure 2:
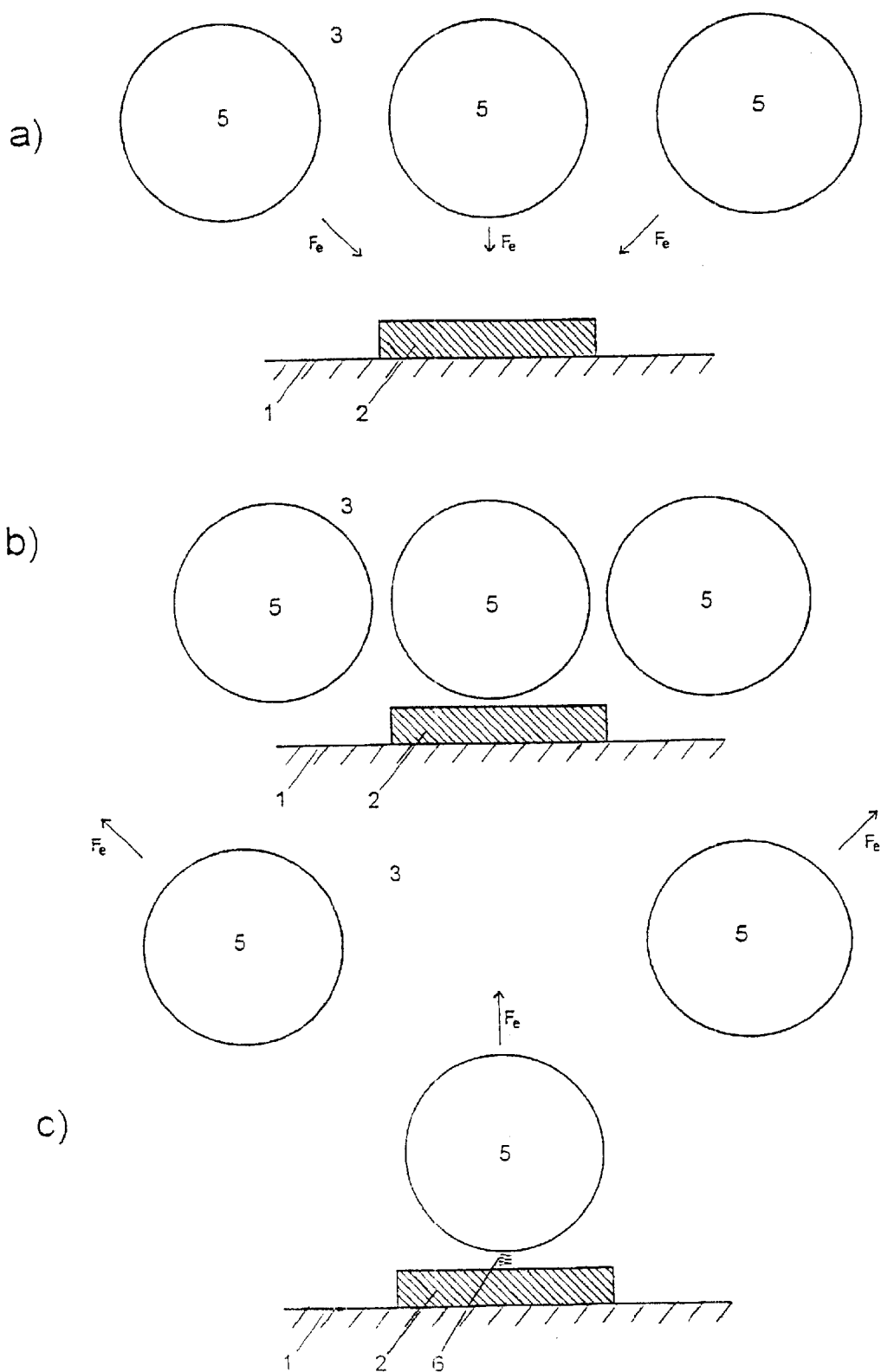

FIG. 2 shows electrophoretic transport of electrically charged marker particles 5 described above in theory. The marker particles 5 are moved in the direction of the microelectrode due to an electrical voltage of, for example 5000 mV, applied between a microelectrode 2 and a counterelectrode not shown, since electrical forces $F_e$ act on the particles (FIG. 2a). After moving FIG. 2b) the marker particles 5 close to the microelectrode 2, there may be binding interaction 6 with the electrode 2 designed as substrate (FIG. 2c). After reversing the electric field, the electrical forces $F_e$ act in the opposite direction, so that the non-bound marker particles 5 are again distanced from the microelectrode 2 (FIG. 2c). A pseudo-washing step takes place in this manner by electrophoretic transport. A selection of materials having different charges, which are suitable for electrophoretic transport, is available for the marker particles 5.

Transport of paramagnetic or diamagnetic marker particles may also take place in a magnetic field, wherein in the case of diamagnetic marker particles the magnetic field has to be inhomogeneous.

The acting principle of marker particle detection and transport underlying the invention may be designated as a field effect induced by marker particles (label particles) (label-induced field effect, LIFE).

Figure 3:
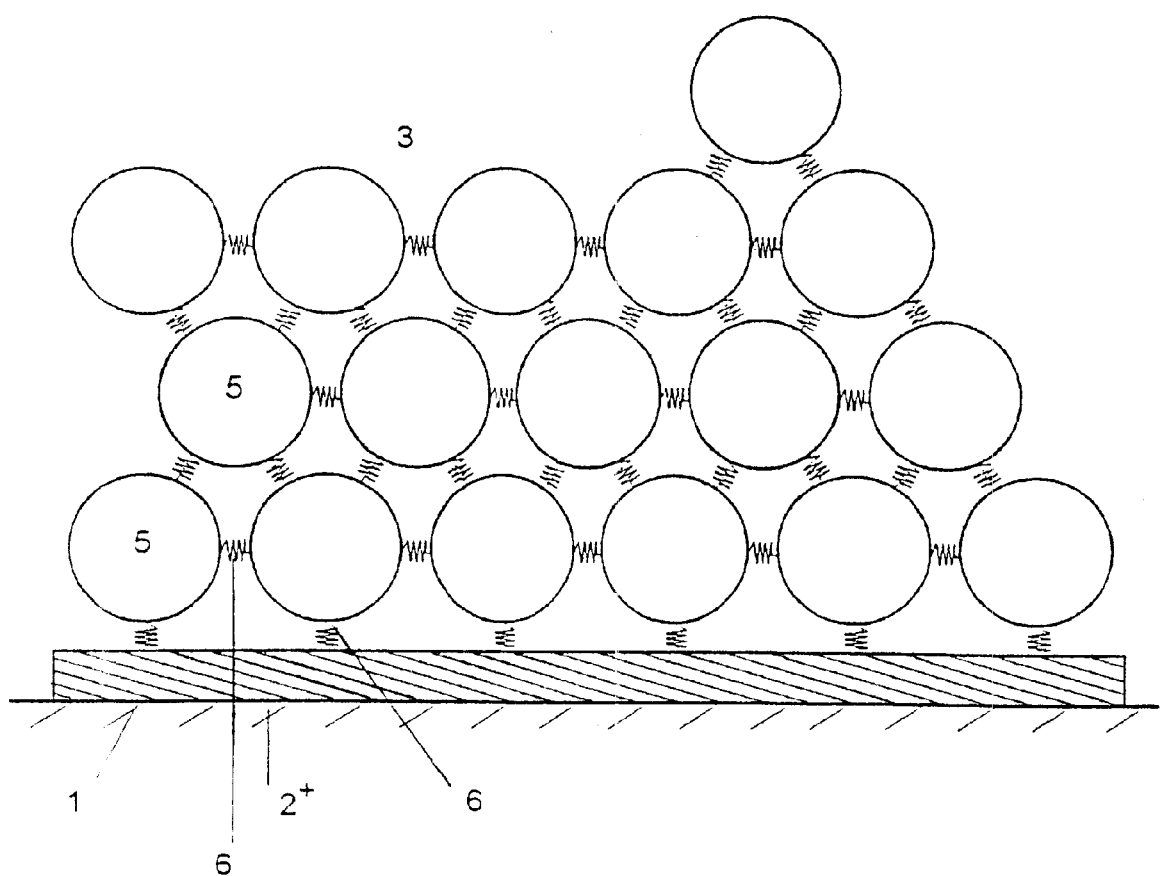

FIG. 3 shows a bioassay for the detection of higher analyte concentrations. So that binding 6 of several marker particles 5 having diameters of about 1 μm may be detected by measuring technology, larger electrodes 2, on the surface of which there is surface covering including three-dimensional agglutination of marker particles, are used on an insulating support 1, for example made from glass. The electrode has, for example a rectangular shape with the dimensions of 10×50 μm.

The measuring range for higher analyte concentrations may be called agglutination range in order to avoid agglutination of marker particles, which are still moved freely in the measuring medium, the measurement may also be assisted here by electrophoretic marker transport to the electrode.

Figure 4:
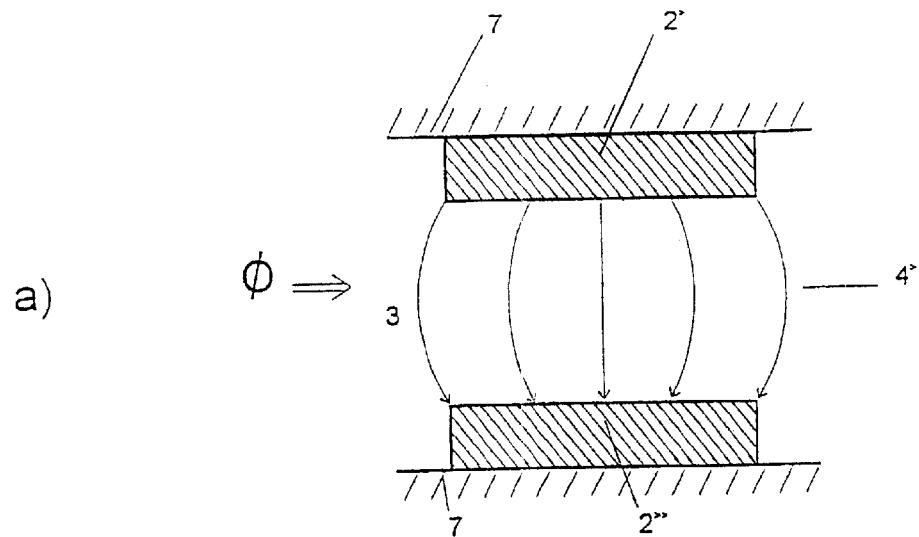
Figure 4:
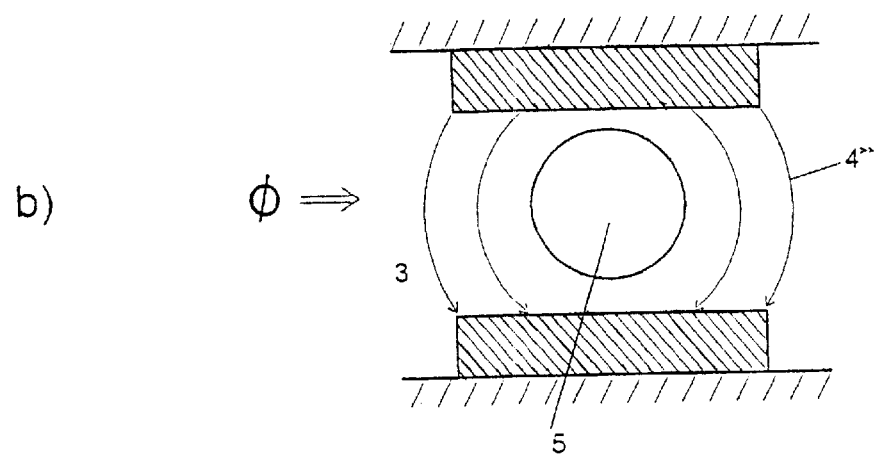
Figure 4:
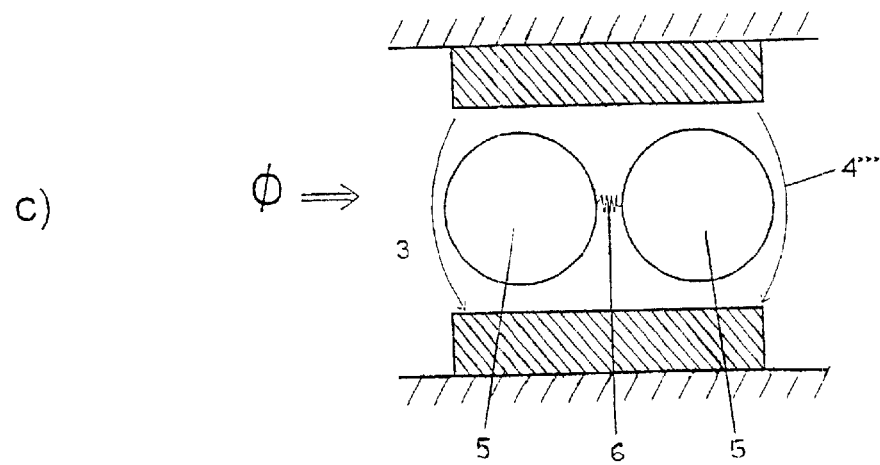

FIG. 4 shows a through-flow cell made from plastic having two opposing microelectrodes $2^>, 2^{>>}$, which consist, for example of platinum, and are applied to support materials 7. The flow φ of a measuring medium 3 moves analyte molecules and marker particles 5 through the through-flow cell. The distance of the microelectrodes $2^>, 2^{>>}$ is 50 μm and the electrode surface in each case 5 μm×5 μm. FIG. 4a) shows the through-flow cell without marker particles, FIG. 4b) with a marker particle 5 and FIG. 4c) with two marker particles 5 bound to one another. The presence of one or more marker particles 5 between the microelectrodes $2^>, 2^{>>}$ may be detected by measuring the electrical resistance, or the complex admittance, due to the electric flow field disturbed due to the marker particles 5.

Figure 5:
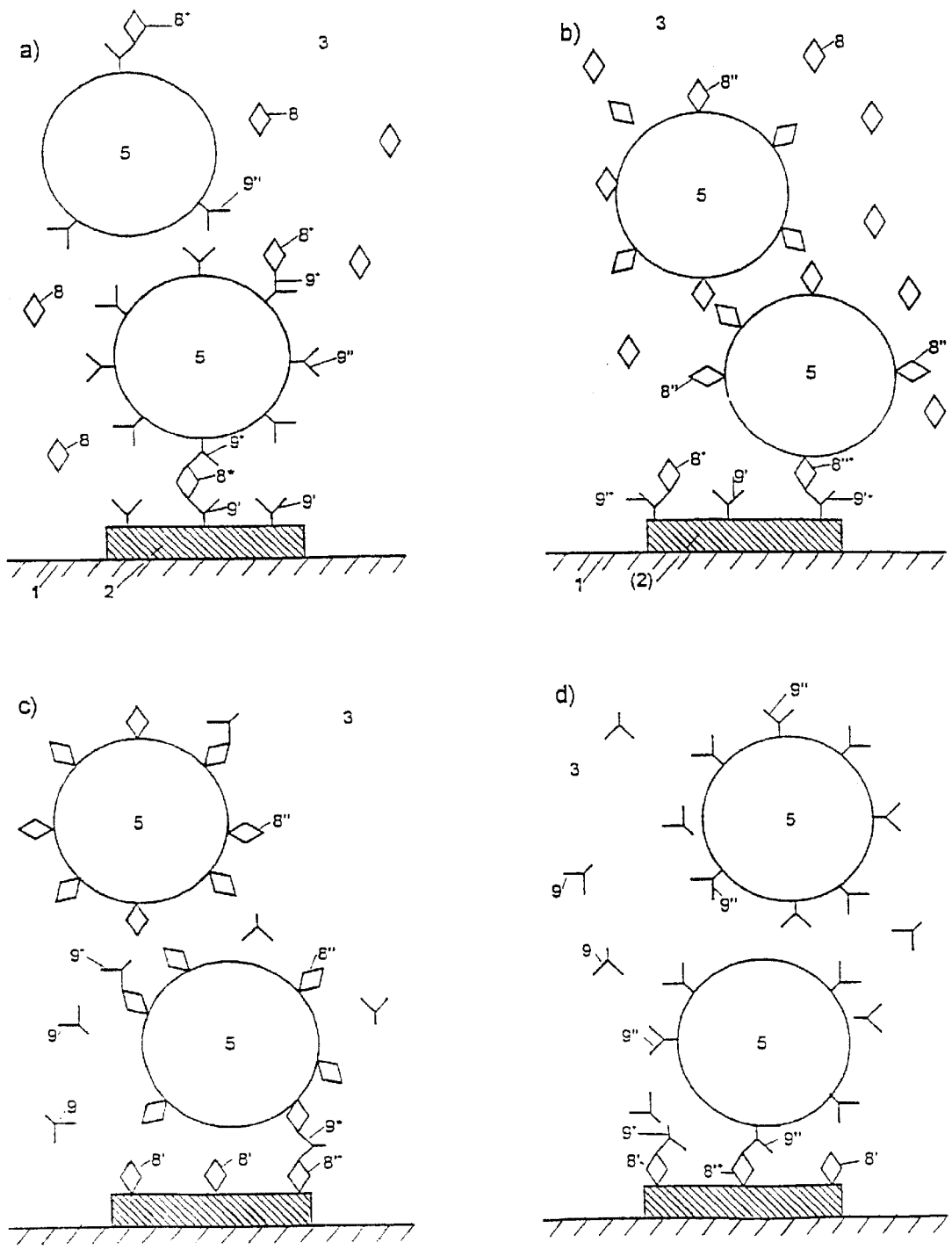

FIG. 5 shows four immunoassay formats according to the LIFE principle.

FIG. 5a) shows an immunoassay for antigen detection according to the sandwich principle. Antibodies 9' are immobilised on an electrode 2. Of the antigens 8, one antigen 8* interacts with an immobilised antibody 9' on the electrode 2. An antibody $9^{(+)}$, which has been immobilised on a marker particle 5, interacts with the antigen 8*, so that a sandwich is formed. The position of the marker particle 5 close to the electrode is detected electrically or electrochemically by marker-induced field effect.

FIG. 5b) shows a competitive immunoassay format for antigen detection. Antigens 8 with antigens 8'' immobilised on the marker particles 5 compete on the antibodies 9' immobilised on a microelectrode 2 In the example shown there is bonding between an immobilised antigen $8''^+$ of a marker particle 5 and an antibody $(9'^+)$ immobilised on the microelectrode 2.

FIG. 5c) shows correspondingly an immunoassay sandwich format for antibody detection and FIG. 5d) correspondingly a competitive format for antibody detection. An exact description is omitted to avoid repetition of the explanations of FIGS. 5a) and 5b).

It is also possible to carry out the measurement, for example according to FIG. 5a—with the aid of two electrodes, of which on one electrode, for example antibodies are immobilised and the other electrode remains free. If the resistances or capacities of both electrodes are now measured against a reference electrode, quantitative recording of the analyte concentration may be determined from the signal difference of both electrodes. Effects which are caused by non-specific binding of molecules can be eliminated in this manner.

Figure 6:
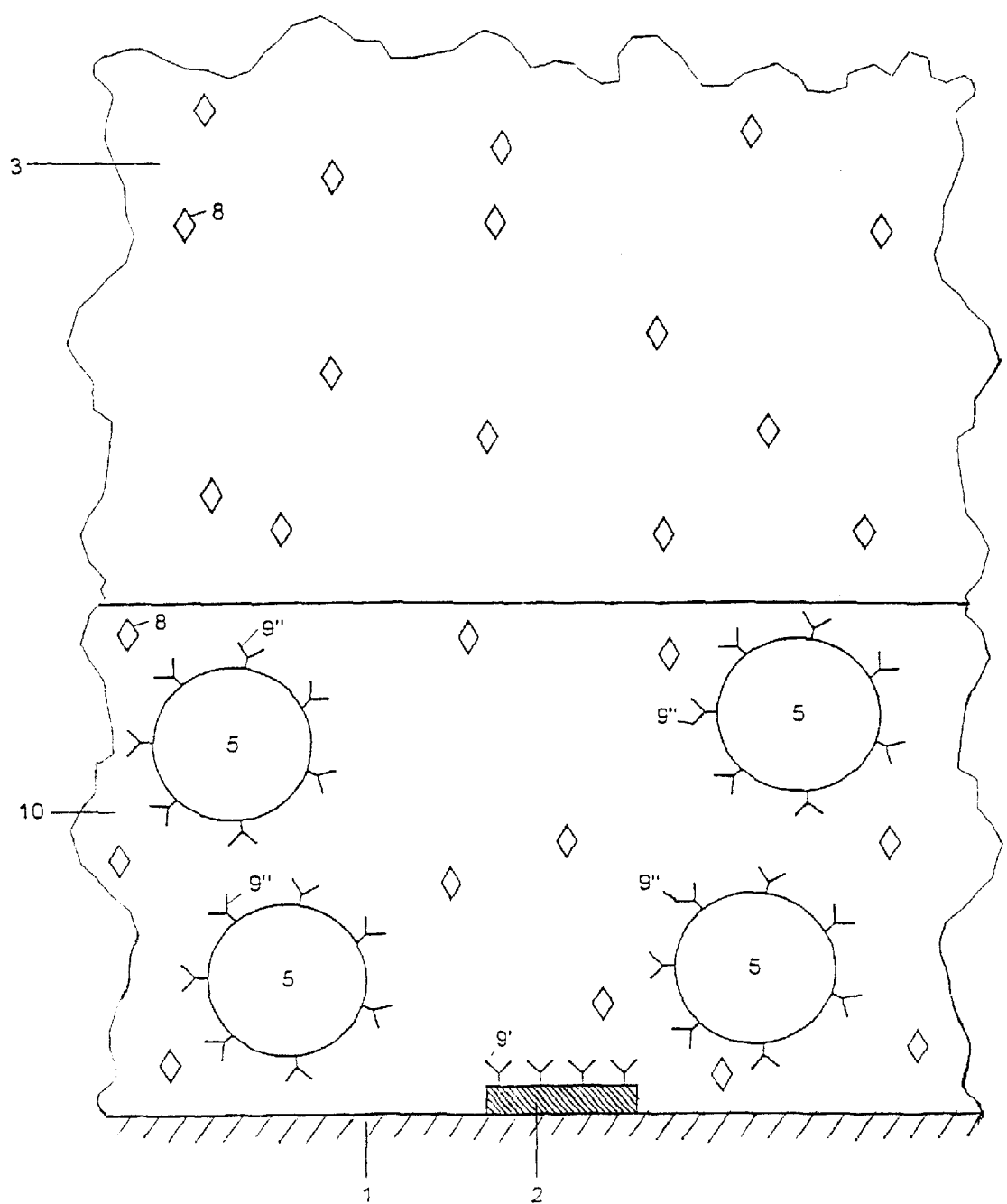

In a further exemplary embodiment, FIG. 6 shows supported by FIG. 5a) an immunoassay format of the sandwich type. In addition to the representation in FIG. 5a), a membrane 10 is arranged here above a microelectrode 2. This membrane consists, for example of nitrocellulose or of nylon. Marker particles 5 with immobilised antibodies 9'' are located and movable in the membrane 10. The detection of antigens 8 may then take place in simple manner in that a liquid measuring medium 3 is applied to the surface of the membrane 10. This membrane may be designed as a functional layer and assumes functions which are known, for example from the field of immunofiltration. The medium experiences filtration and/or conditioning in this membrane. Detection of sandwich formation takes place as described in the example according to FIG. 5a).

However, it is also possible to cover the electrodes with membranes which cannot be penetrated by microparticles. The molecular binding partners are thus not immobilised on the electrode itself, but on the free membrane surface, on which they also interact with the molar binding partner of the marker particles.

Figure 7:
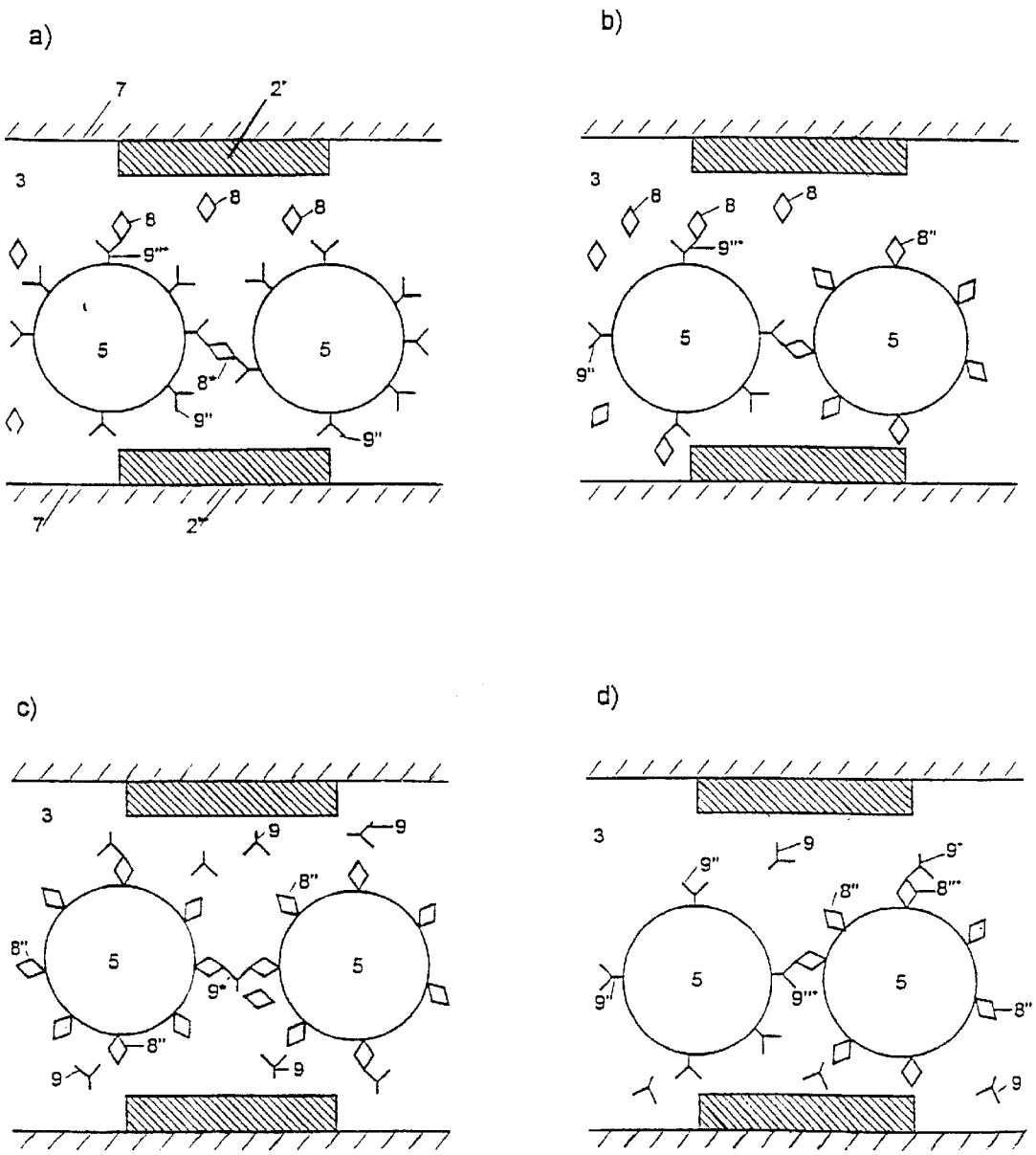

FIG. 7 shows the different immunoassay formats for a through-flow cell with microelectrodes $2^>, 2^>$. FIG. 7a) shows immobilisation of antibodies 9'' on marker particles 5, on which antigens 8 specific to the antibodies 9'' are bound. There is also agglutination of two marker particles 5 via antigens 8*. In FIG. 7b) antigens 8 compete with a marker particle 5, which is provided with antigens 8'', around the binding sites on a marker particle 5 which is provided with antibodies 9''. FIG. 7c) and FIG. 7d) show the corresponding formats for the detection of antibodies. Electrical measurement takes place according to the example of FIG. 4.

Figure 8:
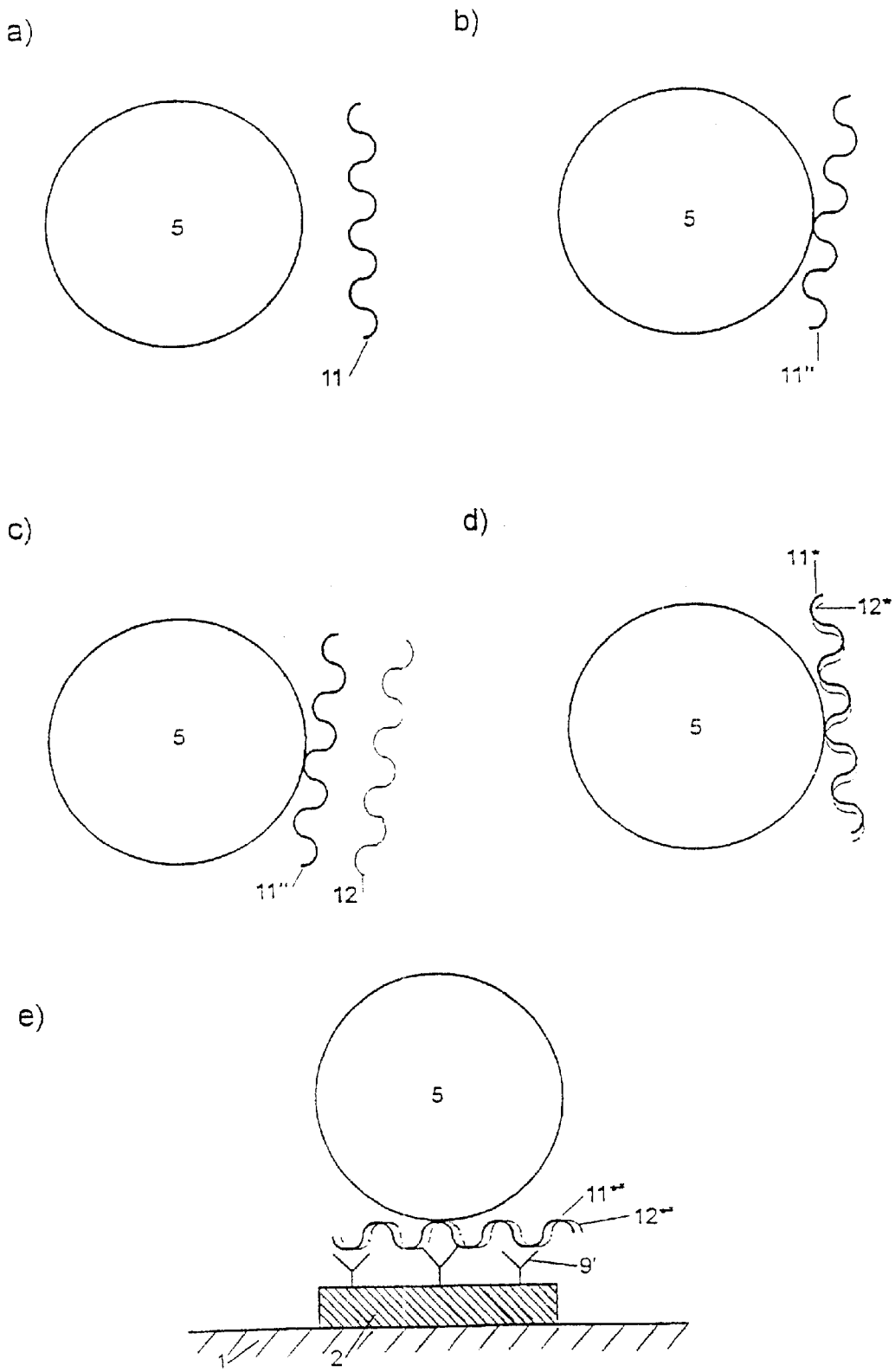

FIG. 8 shows a DNA probe. FIG. 8a) shows a marker particle 5 and DNA 11 in a measuring solution. The DNA 11 is immobilised on a marker particle 5 (FIG. 8b). Then there is hybridisation of DNA 11'' and RNA 12 from the measuring medium (FIGS. 8c,d). In the next step (FIG. 8e) there is interaction between the DNA-RNA hybrid and an immobilised antibody 9', so that the marker particle 5 is located close to the microelectrode and can be detected electrically.

Figure 9:
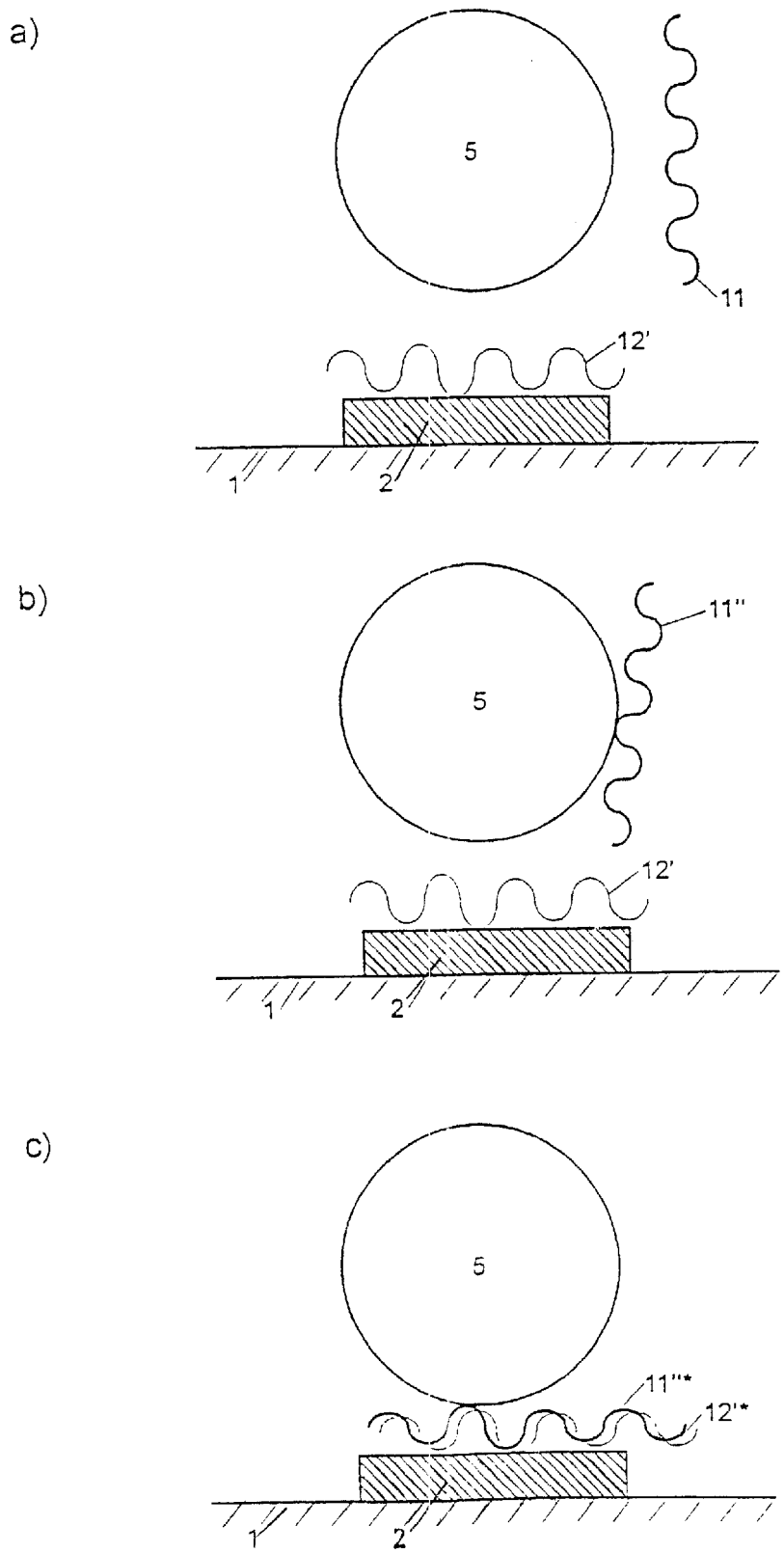

FIG. 9 shows a DNA probe without immobilised antibodies. A DNA molecule 11 is immobilised on a marker particle 5 (FIG. 9a). Following binding of DNA 11 to the marker particle 5, hybridisation is effected with an RNA strand 12' immobilised on the microelectrode 2 (FIG. 9*b*), and there is location of the marker particle 9 near the phase boundary (FIG. 9*c*). In this example RNA molecules may be exchanged for DNA molecules and vice versa.

Figure 10:
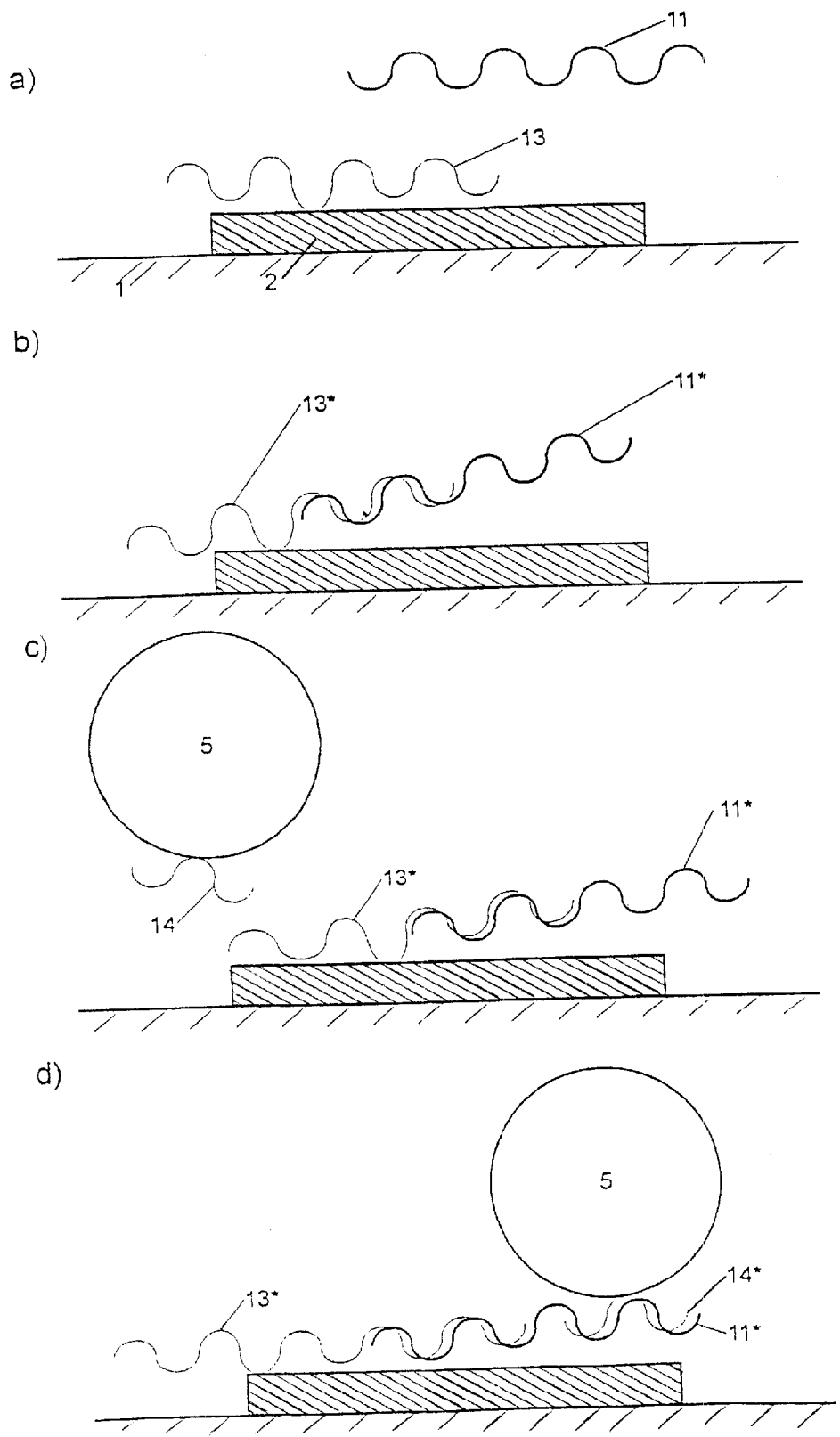

FIG. 10 shows a DNA assay of the sandwich type. A DNA probe molecule 13 is immobilised on an microelectrode (FIG. 10A). A DNA molecule 11 from the measuring medium interacts with the probe molecule 13 (FIG. 10*b*). After hybridisation of molecules 13 and 11 to form a hybrid (11\*, 13\*) there is interaction with a reporter probe molecule 14, which is immobilised on a marker particle 5 (FIG. 10*c*).

As a result of this hybridisation there is location of the marker particle 5 close to the microelectrode (FIG. 10*d*). Recording in terms of measuring technology takes place as described in the previous examples. For example DNA probe arrays for sequencing can be constructed in this manner.

Figure 11:
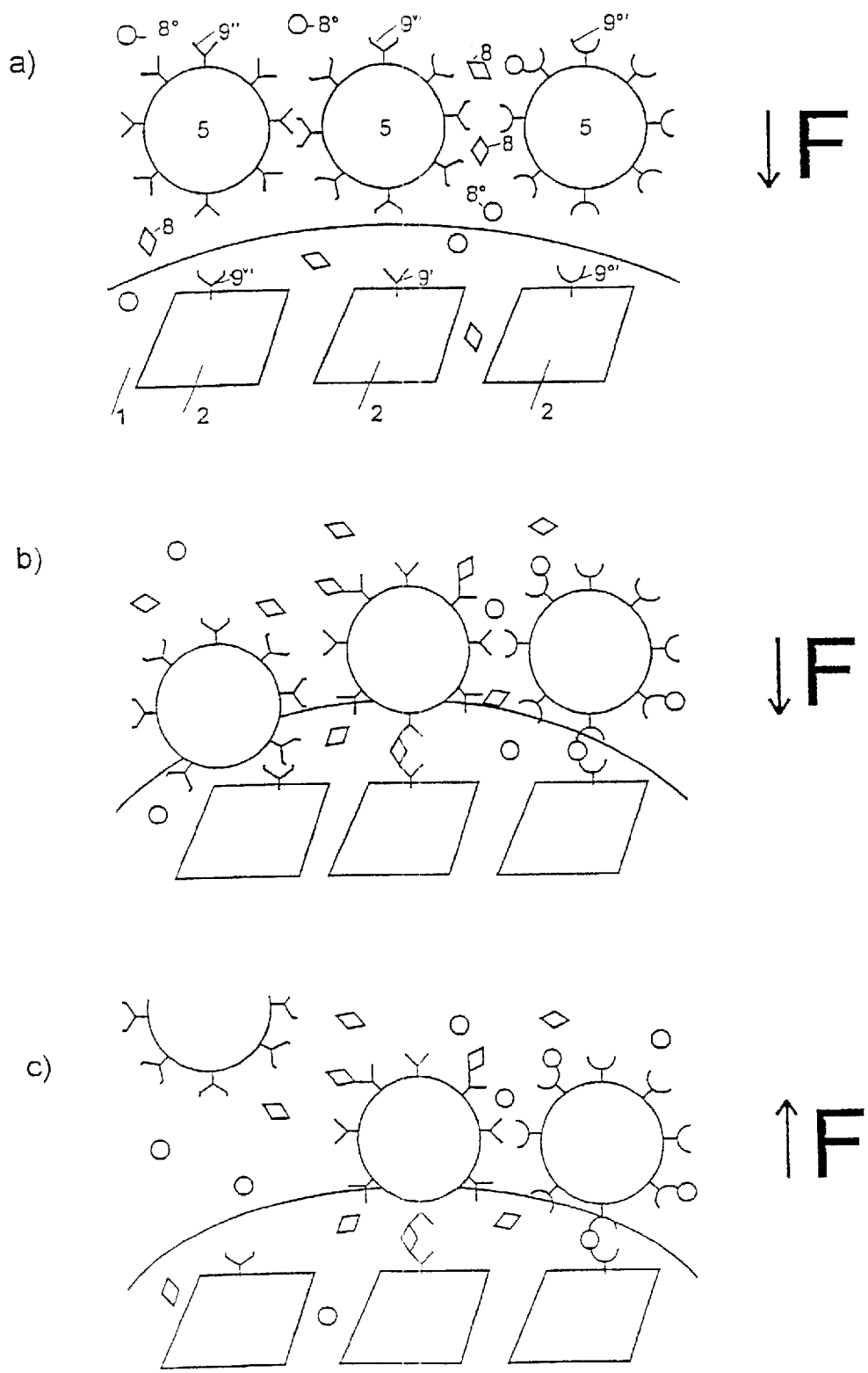

FIG. 11 shows a cutout of a microelectrode array. A plurality of microelectrodes 2 are realised on an insulating support 1. FIG. 11 shows three microelectrodes. Antibodies of different type 9', 9°', 9''' are immobilised on the microelectrodes (FIG. 11*a*). Antigens 8 match antibodies 9'. Antigens 8° match antibodies 9°'. If the said antigens 8, 8° interact with antibodies 9', 9°', which are immobilised on the different microelectrodes, by adding corresponding antibodies, which are immobilised on marker particles, in each case a sandwich may be formed (FIG. 11*b*). Sandwich formation may be assisted in that when using charged marker particles, the latter are moved, by applying an electric voltage between the microelectrodes 2 and an external reference electrode not shown, electrophoretically in the direction of the microelctrodes (FIG. 11*a*) and *b*). After sandwich formation (FIG. 11*b*), electrophoretic transport is reversed by reversing the polarity of the electric voltage and the force F, so that the non-bound marker particles are moved away from the microelectrodes (FIG. 11*c*). This is also a pseudo-washing step. Recording of the marker particles bound in the sandwich takes place electrically, as described in the preceding examples. The electrophoretic marker particle transport may also be replaced by magnetically induced transport of paramagnetic marker particles.

In the same manner using such arrays, a DNA chip assay may be realised which may be used for sequencing by hybridisation. DNA probes are thus used instead of antibodies or antigens, as shown in FIGS. 8 to 10.

Figure 12:
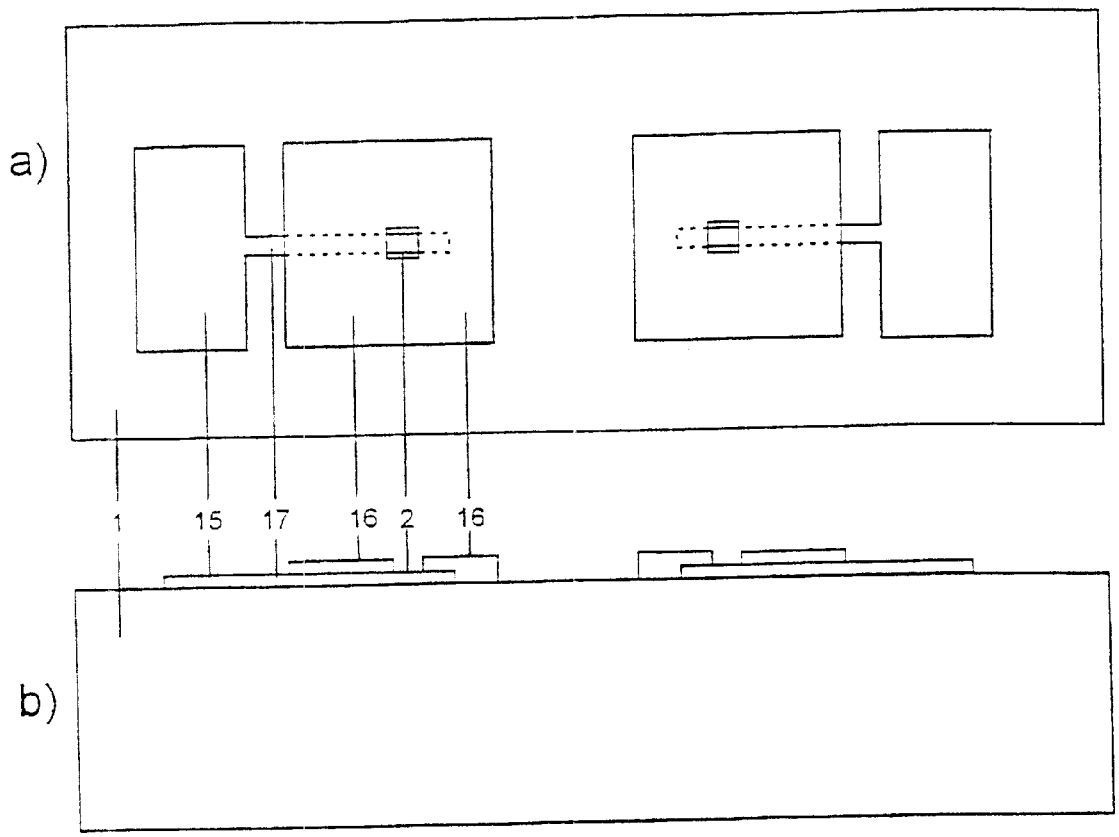

FIG. 12 shows a cutout from a planar microelectrode array. A support 1 consists of glass. A microelectrode 2, a conductor strip 17 and an electrical contact 15 consist of platinum and have been produced by a conventional thin-layer process. The media (marker particles, antibodies etc.) used for such a bioassay and the measuring medium may be applied to the microelectrode.

Figure 13:
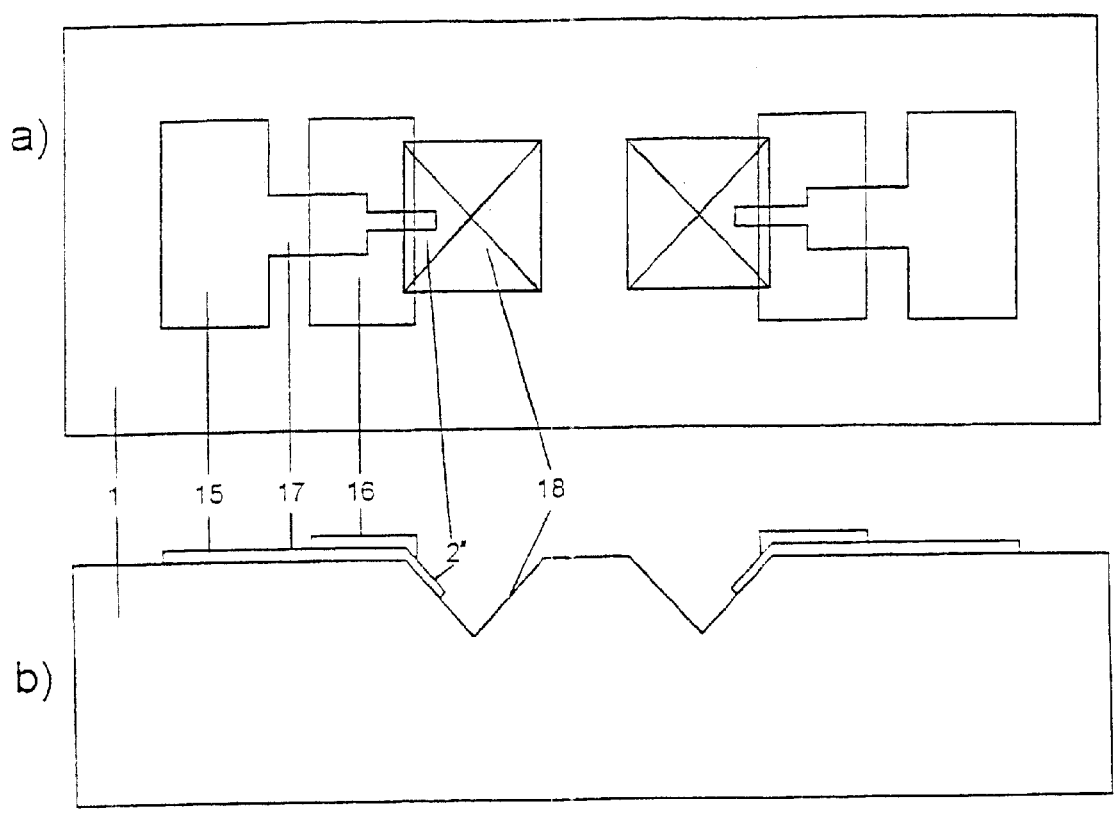

A further exemplary embodiment is shown in FIG. 13. A mirror-symmetrical structure, and therefore only provided with reference numbers on one side, having two microelectrodes 2# is shown as a cutout from a larger array. A support 1 for the microelectrodes 2# consists of a material which can be structured three-dimensionally. Silicon in particular can be used for this and is structured three-dimensionally by known anisotropic etching processes. The silicon is electrically insulated on the surface. $SiO_2$ layers are produced on the silicon surface for this by thermal oxidation.

In addition, an $Si_3N_4$ layer may be deposited above the $SiO_2$ layer by CVD processes. A metal film may be deposited and structured on the support surface with the aid of introduced thin-layer processes. This metal film consists of platinum. After structuring, a microelectrode 2# is produced which is connected to an electrical connection contact 15 via a conductor strip 17. The conductor strip 17 is covered with an electrical insulation layer 16, which consists, for example of a polymer material. The microelectrode 2# is situated in a pyramid-like depression, which may be designated as containment 18. The containments 18 serve on the one hand for receiving the material to be immobilised, on the other hand they serve for receiving the sample. Operation of such an array may take place in the same manner as in the example according to FIGS. 11 and 12.

Figure 14:
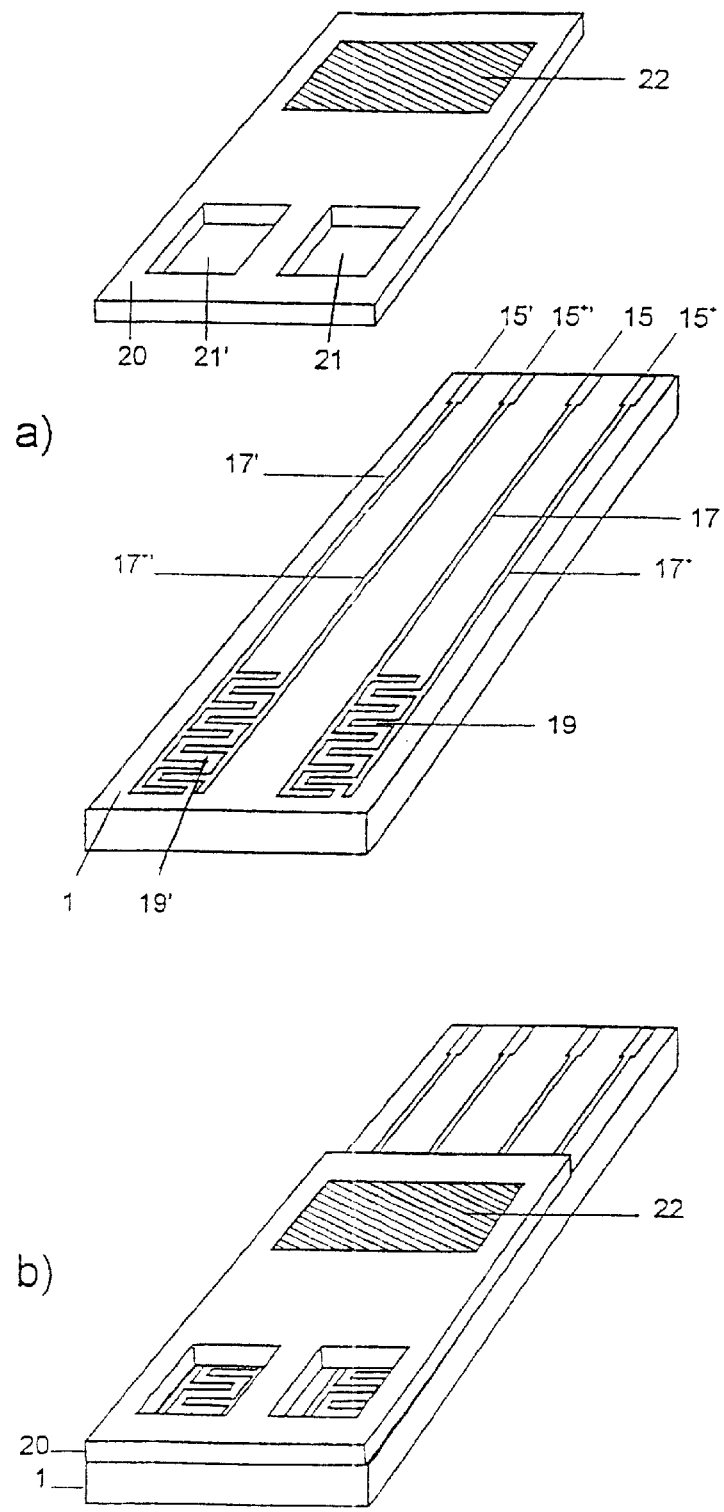

FIG. 14 shows a simple structure for a device according to the invention as a bioassay. Two interdigital structures 19 and 19' are realised on a support 1 (FIG. 14*a*). The finger structures shown are not shown to scale. The finger widths and the distances between the fingers are typically a few $\mu$m. Hence, the requirement of a small electrode surface for detection of only a few bound marker particles is provided. The interdigital structures 19, 19', electrical conductor strips 17, 17⁺, 17', 17⁺' and electrical connection contacts 15, 15⁺, 15', 15⁺' are produced from platinum, for example with the aid of known thin-layer processes. This support is provided with a covering 20 (FIG. 14*b*). Mounting of the covering 20 takes place, for example by adhering. It may also be applied by the screen printing process. The sample may interact with the interdigital structures through perforations 21, 21' provided in the covering. Antibodies have been immobilised beforehand on the surface of one of the interdigital structures. An immunoassay of the sandwich type may be carried out by immersing the structure according to FIG. 14*b*) in a measuring solution with antigens to the immobilised antibodies as analytes, as described in FIG. 5*a*). Marker particles with immobilised antibodies are weakly immobilised on the surface 22 for this. After the structure according to FIG. 14*b*) has been immersed in the measuring medium as far as the upper edge of the surface 22, the marker particles situated on the surface 22 may be released in the measuring medium. Sandwich formation may take place in this manner, as described in FIG. 5*a*).

Figure 17:
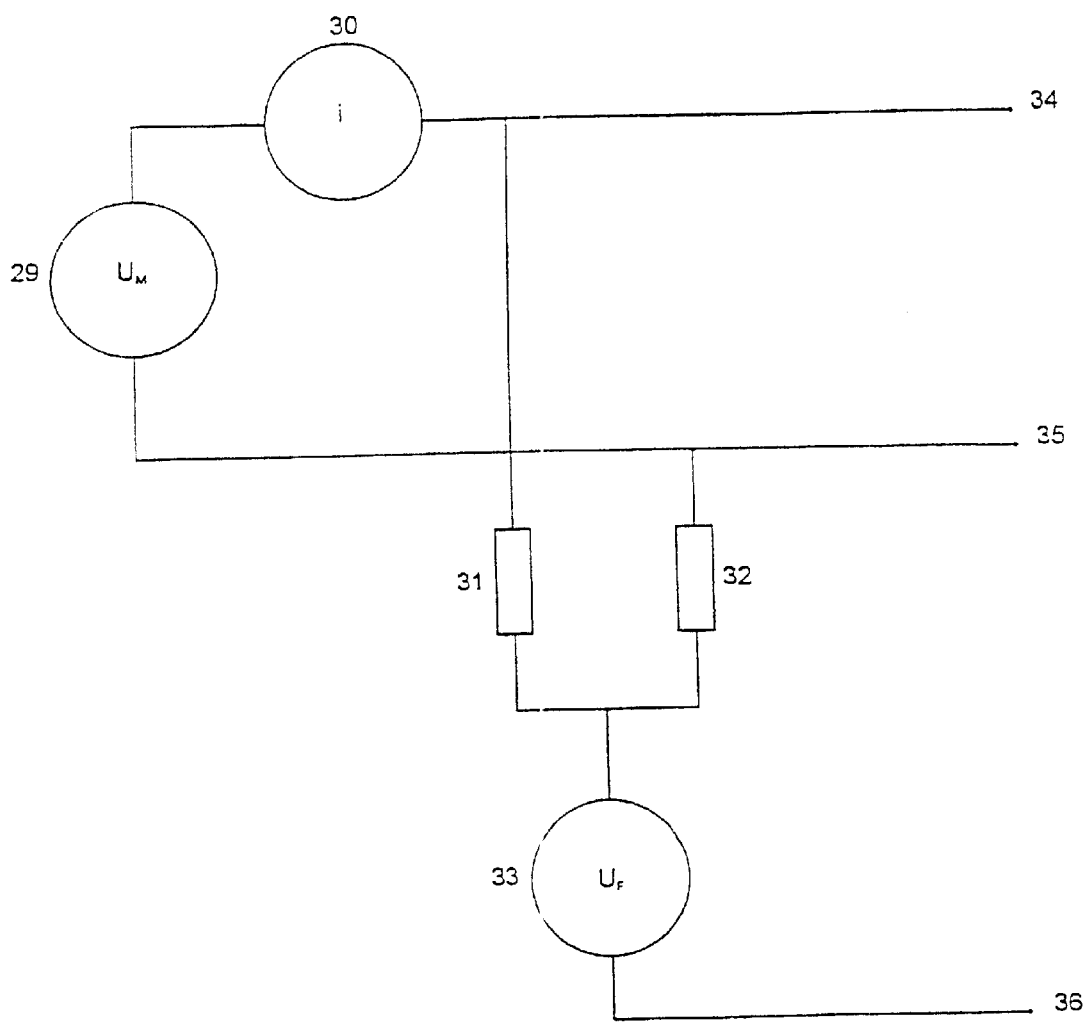
FIG. 17 Measuring circuit for assays according to FIGS. 14 to 16

In addition, it is possible, to carry out electrophoretic transport of charged marker particles by applying an electric voltage between the interdigital structures and an external reference electrode. An electric circuit for this is shown in FIG. 17, which is described further below.

The measurement may be carried out on both interdigital structures. Since antibodies are only immobilised on one of the two structures, there is also only sandwich formation here. The influence of non-specifically binding molecules may be eliminated by evaluating the difference of the signals from the two interdigital structures.

Figure 15:
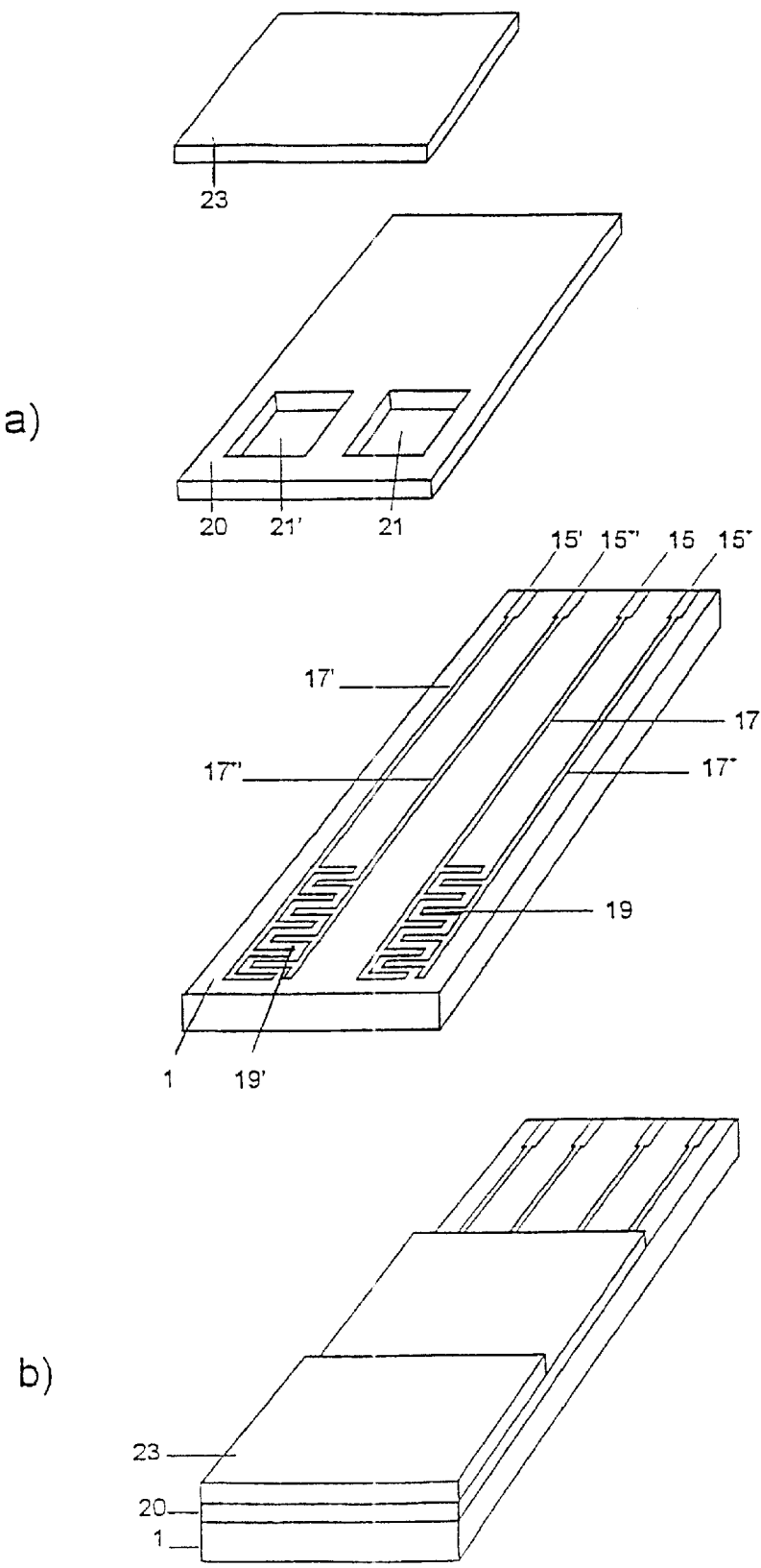

FIG. 15 shows an exemplary embodiment modified with respect to FIG. 14. Here the covering 20 with the perforations 21, 21' (FIG. 15*a*) is covered by an additional membrane 23 (for example a dialysis membrane (FIG. 15*b*). The marker particles with the immobilised molecules used for the bioassay have been introduced in soluble form into one of the perforations 21, 21' before applying the membrane 23. The sensor configuration according to FIG. 15*b*) is immersed in the measuring medium with its lower end, so that the measuring medium may penetrate through the thin layer 23 into the region of the perforations 21, 21' The measurement is carried out as described in the example according to FIG. 14.

In a further exemplary embodiment, it is possible to replace electrophoretic transport of the marker particles by magnetic transport. This is shown simplified in FIG. 16, in which an assay structure according to FIG. 14 is provided with a magnet 24. To assist sandwich formation, a magnetic field is designed so that the paramagnetic marker particles are drawn into the region of the interdigital structures 19, 19'. This is possible, for example with the aid of the small magnet 24. After sandwich formation, the magnet 24 is arranged on the opposite side (in FIG. 16 above the assay structure), so that the marker particles are moved away from the interdigital structures 19, 19' and there is a pseudo-washing step.

The small magnet 24 may also be replaced by an electromagnet.

Figure 16:
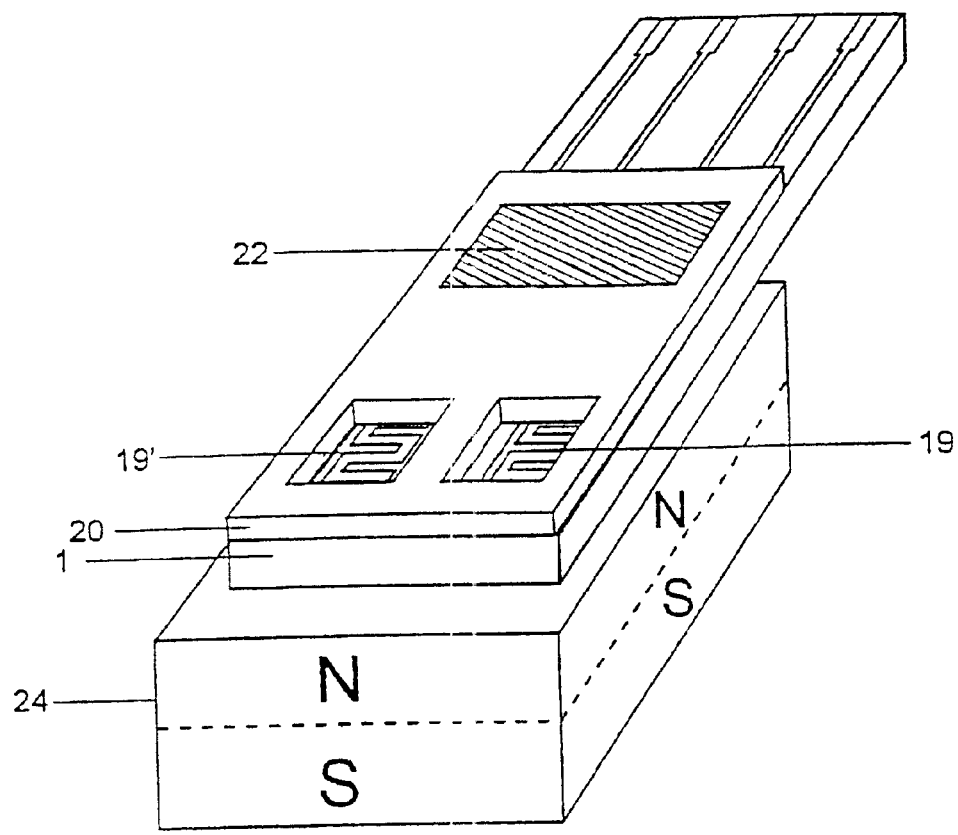
FIG. 16 Modified assay according to FIG. 14

FIG. 17 shows a measuring circuit for devices (assays) according to FIGS. 14 to 16. A voltage source 29 produces a direct voltage or an alternating voltage signal in the mV range, preferably at the level of a few 100 mV. This signal is connected via connections 34 and 35 to connections 15 and 15+ or 15' and 15+' of the interdigital structures according to FIGS. 14, 15 or 16. The direct current or alternating current being adjusted via the measuring solution is recorded using a current meter 30. The electrical conductivity value as a measure of the analyte concentration of the measuring medium in the surroundings of the electrodes of the interdigital structure optionally covered with marker particles is measured from the voltage-current data.

A direct voltage in the range of a few 100 mV against a counter-electrode may be applied for electrophoretic marker particle transport by a direct current source 33 via resistances 31 and 32 at the connections 34 and 35. The counter-electrode may be situated at a greater distance from the interdigital structures in the measuring medium. By way of example this counter-electrode consists of a chloridised silver film, as corresponds to the state of the art. The values of the resistances 31, 32 lie in kΩ—or in the MΩ—range (for example at 100 kΩ).

Figure 18:
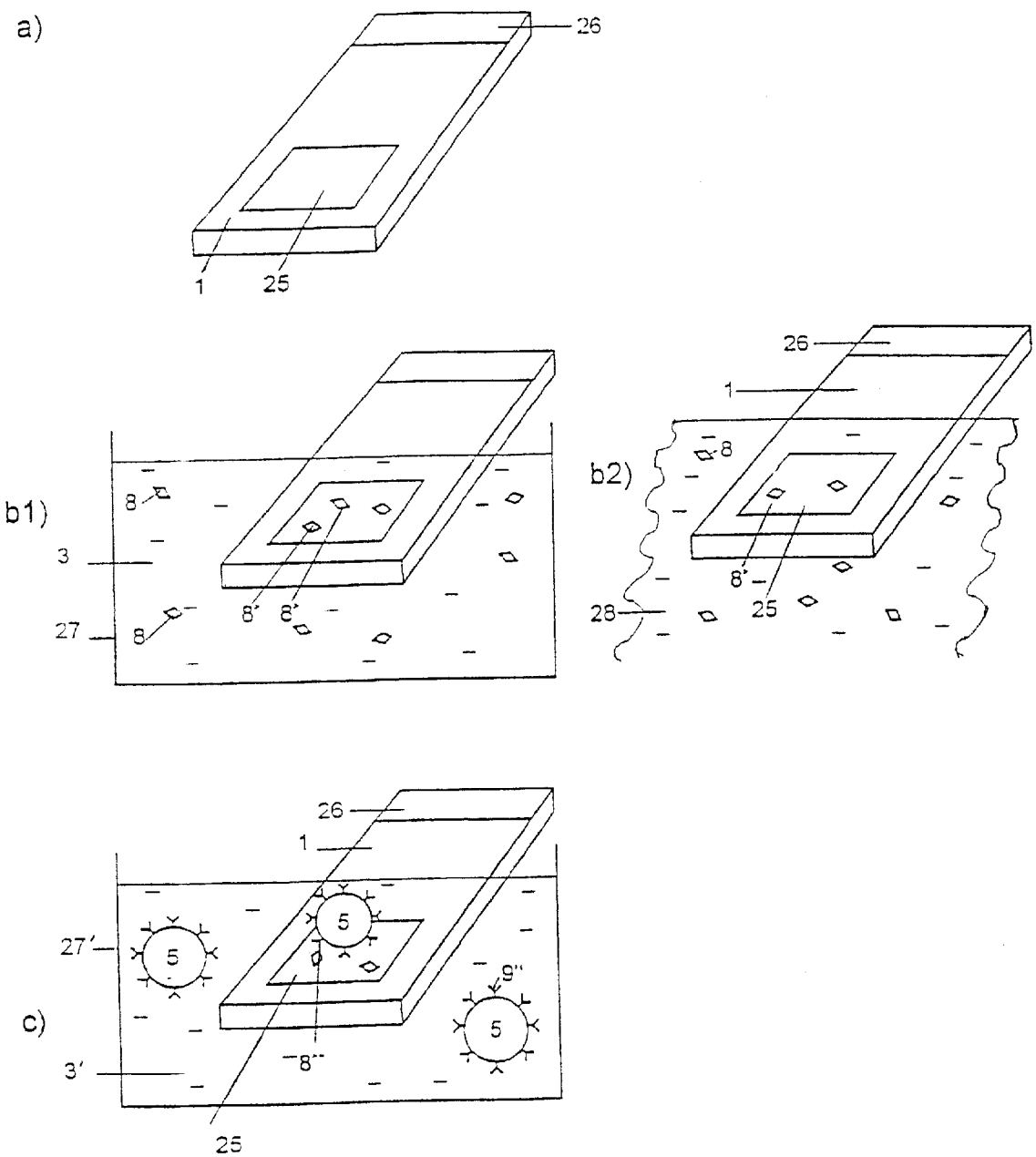
FIGS. 18*a*–*c* Immunoassay test rods

FIG. 18 shows an immunoassay test rod in greatly simplified form. An immobilisation layer 25 made from a material, on the surface of which antigens are immobilised on contact, is situated on a support 1 (FIG. 18a). This layer consists of PVA and covers an interdigital double structure (not shown), as are known from FIGS. 14 to 16. The electrical connections (not shown) are situated on a connection surface 26. If the arrangement according to FIG. 18a is introduced into a vessel 27 with a measuring medium 3 containing antigens 8, antigens are immobilised on the immobilisation surface 25 (FIG. 18b1). The same may occur when introducing the arrangement according to FIG. 18a into a tissue (for example flesh . . . ) or a gel-like measuring medium (FIG. 18b2).

The arrangement is then contacted with a liquid medium containing marker particles with immobilised antibodies (FIG. 18c). After the antibody/antigen interaction is established with location of the marker particles close to the electrode (in the region of the interdigital structures under the layer 25), the measurement may be earned out as shown in the preceding examples.

Figure 19:
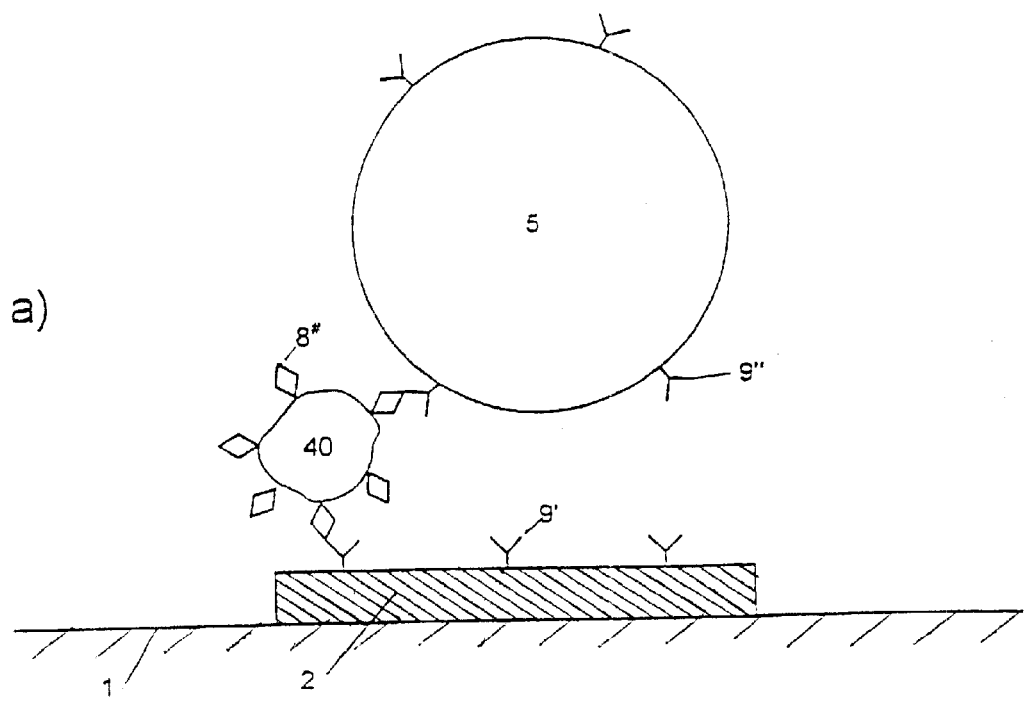
FIGS. 19*a*–*b* Bioassay for whole cells
Figure 19:
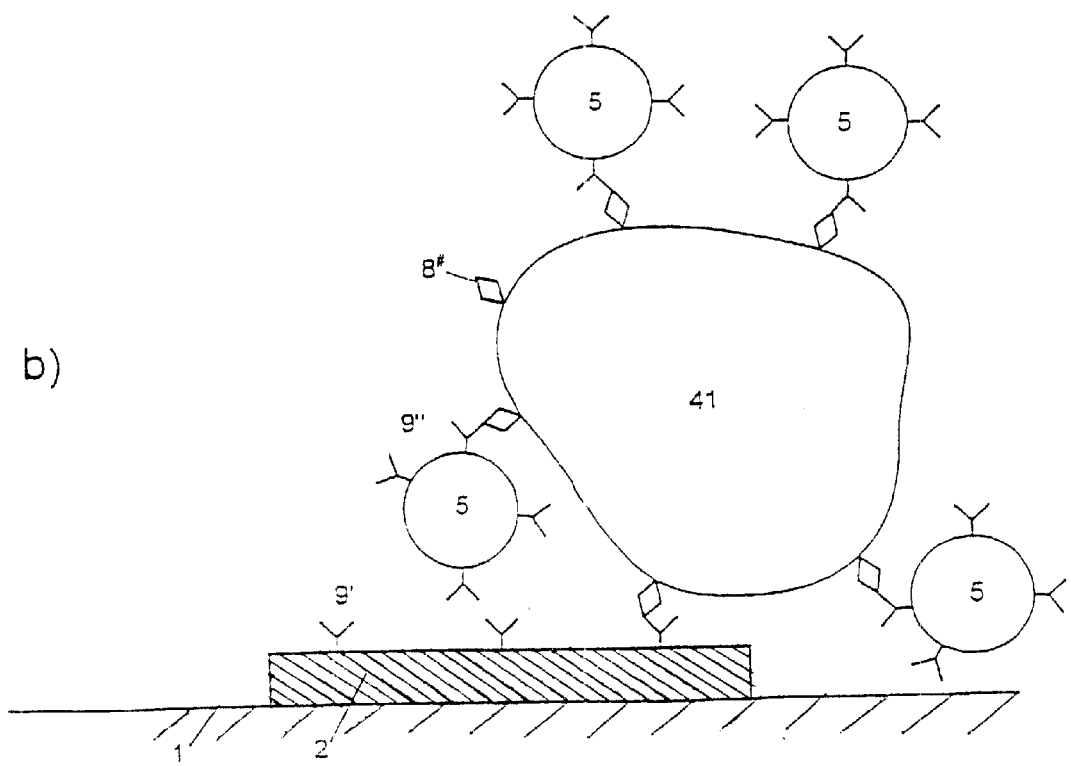

A further example of a bioassay is shown in FIG. 19. Whole cells 40 can be detected using such an assay. The arrangements according to FIGS. 19a) and b) correspond to an immunoassay format according to FIG. 5a). Compared to the immunoassay, the antigens are replaced by cells 40 which support at their surface structures having the property of antigens $8^{\#}$. FIG. 19a) shows a bioassay with small cells (for example protocytes having diameters in the range from 0.3 and 2.5 $\mu$m). FIG. 19b) shows an assay with, for example eucytes having diameters between 2 and 20 $\mu$m.

The marker particles used in the preceding exemplary embodiments may consist, for example of microspheres of $SiO_2$, latex, diamagnetic, paramagnetic and other materials having diameters between 15 nm and 25 mm. Furthermore, dendrimers may also be used.

In addition to marker particles made from electrically insulating materials. marker particles can also be used which are produced from metallic material. Such electrically conductive marker particles can also be realised by electrically insulating marker particles (for example microspheres) being subject to vapour-deposition with a thin metal layer.

Figure 20:
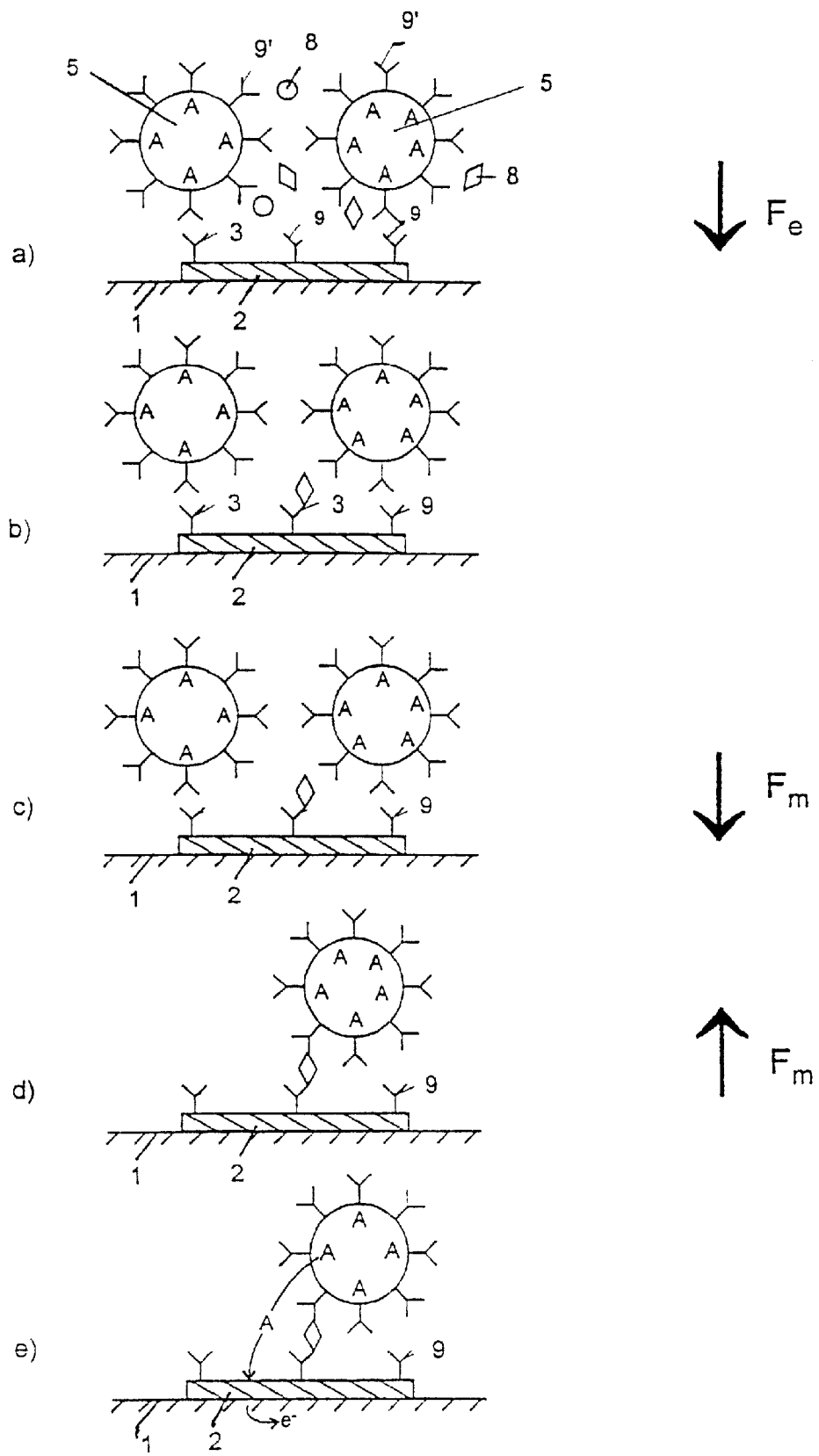
FIGS. 20*a*–*e* shows further embodiments of immunoassay formats

FIG. 20 shows as a further exemplary embodiment a further immunoassay format. A microelectrode 2, on which antibodies 9 are immobilised, is situated on the support 1, as in all preceding exemplary embodiments. As shown in FIG. 2a, antigens 8 and 8' as well as marker particles 5 are situated in the half-space above the microelectrode. These marker particles are charged with an electroactive material A (for example ascorbic acid). The antigens 8, 8', which are complementary to the antibodies 9 on the electrode 2, may interact in binding manner. If the antigens carry an electric charge, it is additionally possible to convey these antigens to the electrode with the aid of an electric field $F_e$ (FIGS. 20a+b). The marker particles 5 having a magnetic or paramagnetic core may now be moved towards the electrode 2 with the aid of a magnetic field $F_e$ (FIG. 20c). The antibodies 9 may thus interact in binding manner with the antigens 8 which have already been bound to the antibodies which are immobilised on the electrode 2. Non-bound marker particles may be removed from the microelectrode 2 with the aid of a directionally turned magnetic field $F_m$. The marker particles 5 are charged with the electroactive material A which may emerge from the marker particle surface by diffusion. Hence, binding of marker particles close to the electrode is recorded in that conversion of the electroactive material A takes place at the electrode 2, in which electric current flows in the form of electrons C. An electric voltage of a few 100 mV is thus applied between the microelectrode 2 and a counter-electrode (not shown). An electric field for electrophoretic transport may be used alternatively to move the marker particles with the aid of a magnetic field. This has already been shown in the preceding exemplary embodiments.

Figure 21:
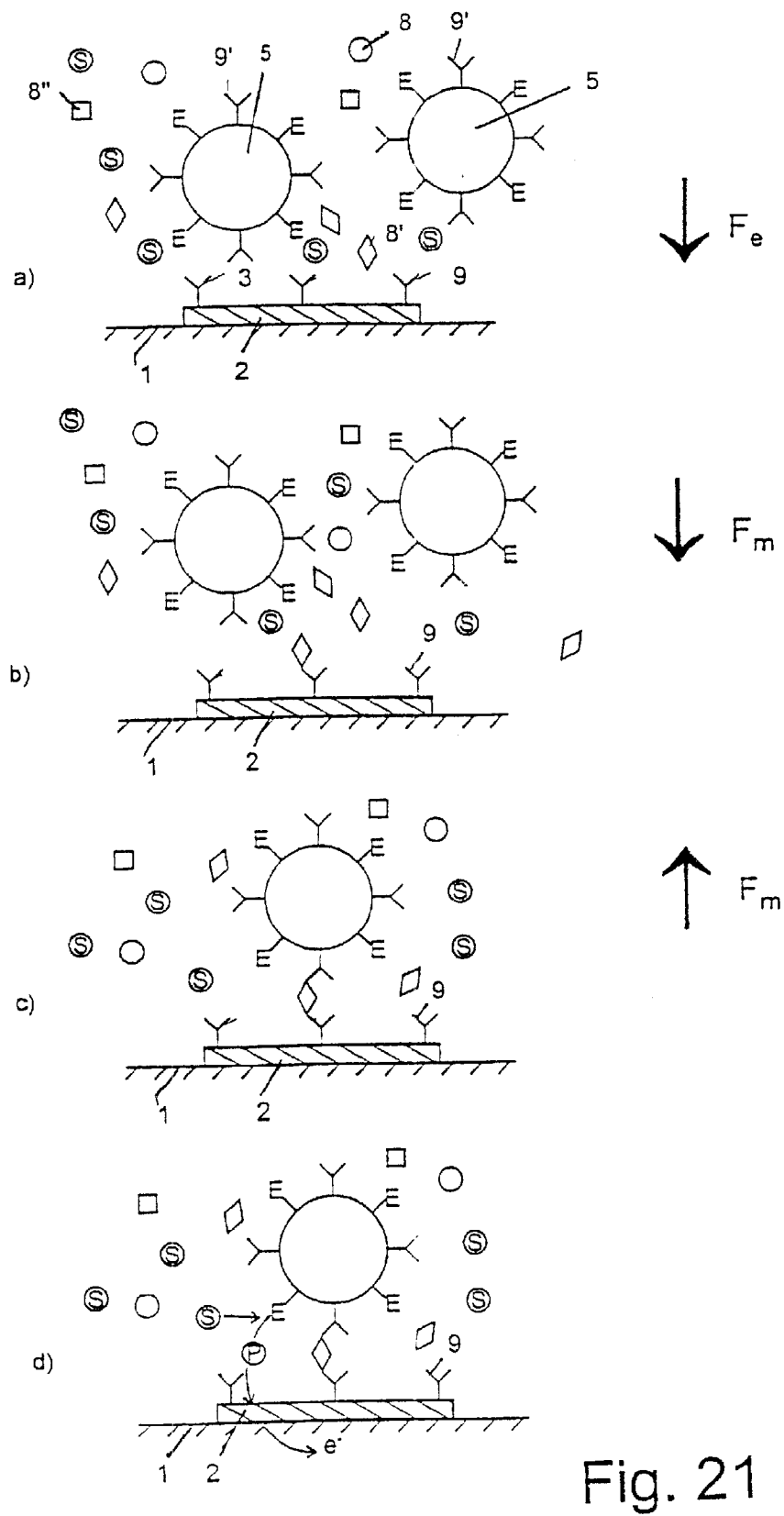
FIGS. 21*a*–*d* shows further embodiments of immunoassay formats

A further exemplary embodiment is shown in FIG. 21. Here there is binding interaction of antigens 8' with antibodies 9, which are immobilized on the electrode 2, as in the example according to FIG. 20. This may also be assisted again by an electric field $F_e$.

In this exemplary embodiment, not only antibodies 9' but also enzymes E are immobilised on the surface of the marker particles 5. A substrate S (for example glucose) which may be reacted enzymatically with the aid of an enzyme (for example glucose oxidase), is situated above the electrode 2 in the measuring medium. if there is now binding of the marker particles to the surface of the electrode 2, the enzymes (E) immobilised on the marker particle surface lead to conversion of the substrate (S). The product (P) thus produced (for example $H_2O_2$) may be reacted electrochemically on the electrode surface 2.

Excess marker particles may be removed from the electrode surface by reversing the magnetic field $F_m$.

The enzymatically catalysed material conversion at the electrode 2 is effected in the same manner as for known electrochemical glucose sensors. An electric voltage of a few 100 mV (preferably 600 mV) is applied for this between the electrode 2 and a counter-electrode.

Figure 22:
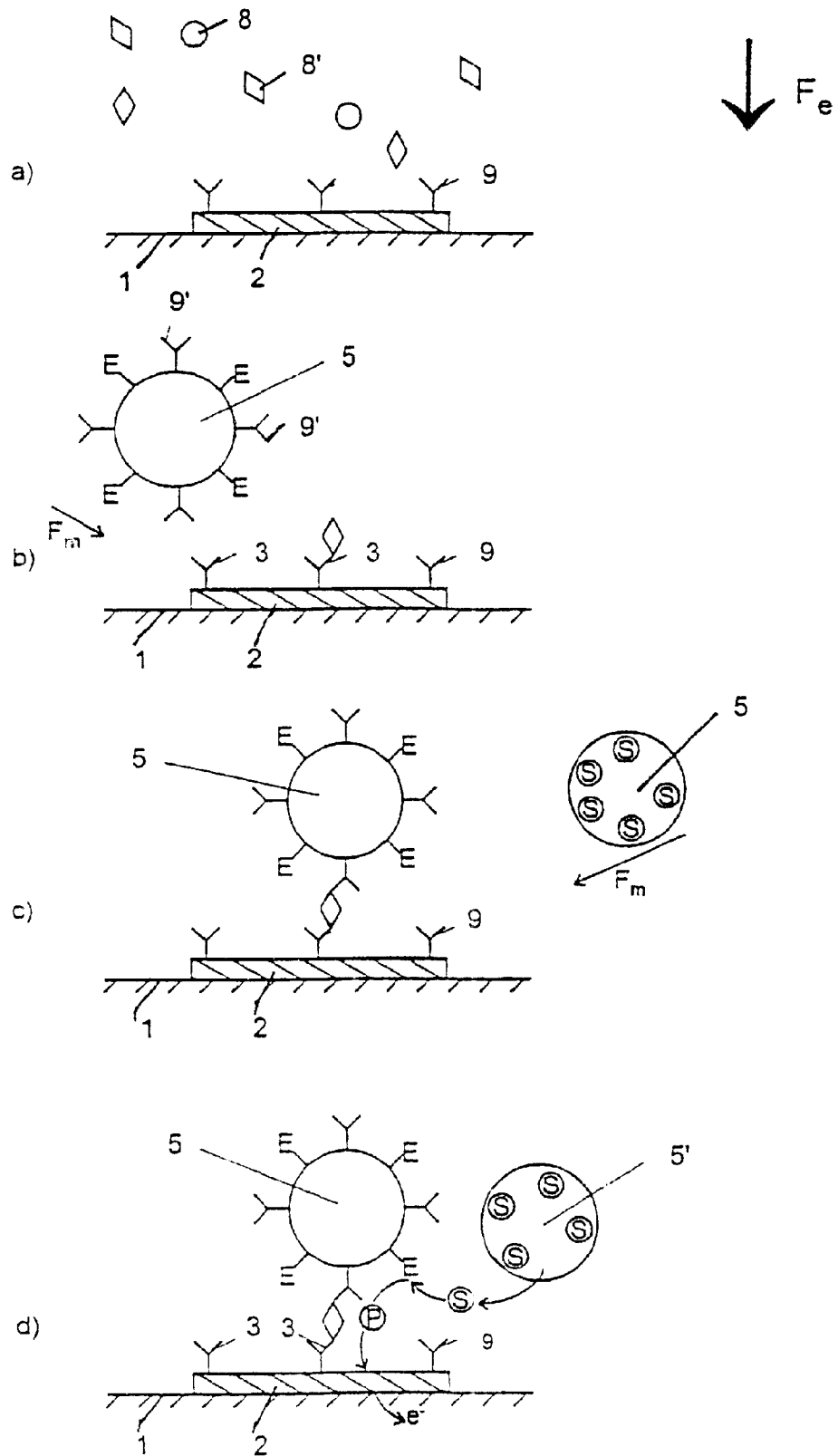
FIGS. 22*a*–*d* shows further embodiments of immunoassay formats

A further exemplary embodiment is shown in FIG. 22. Here there may also be, as in the preceding exemplary embodiments, binding interaction between antigens 8, 8' and the antibodies 9 immobilised on the electrode. Marker particles may now be transported to the vicinity of the electrode with the aid of a magnetic field. The marker particles 5 support immobilised antibodies 9 and immobilised enzymes (E) on their surface (FIG. 22b). After there has been binding interaction between the marker particles 5 and the electrode 2, the excess of marker particles 5 (not shown) may be distanced from the electrode by reversing the magnetic field. A second type of marker particles 5' is then moved to the electrode 2 with the aid of a magnetic field $F_m$. These marker particles 5' are charged with a substrate S (for example glucose). If the marker particles 5' are situated near the electrode 2, a substrate S diffusing out leads to interaction with the enzymes E immobilised on the marker particles 5. The product P thus produced is reacted electrochemically at the electrode 2, as shown in the preceding exemplary embodiment (FIG. 22d).

Marker particles, which are charged with enzymes, may also be used instead of marker particles with immobilised enzymes (FIG. 21 and FIG. 22). The enzymes may be released from these marker particles in the same manner as has been described for the electroactive substance in the example according to FIG. 20.

Analogously, DNA probes and other bioassays can also be realised apart from the immunoassay formats shown above. Only the immunocomplexes are thus replaced by other bonds.

Also in the variants according to FIGS. 20–22, assays having an extremely low detection limit can be realised if the surface area of the microelectrode is not very much greater than the projected cross-sectional surface area of the marker particles. Hence individual binding detection is also possible here, that is binding of a marker particle to a microelectrode can be detected.

In these variants, detection is based on the fact that the marker particles cause an increase in material concentration in their immediate surroundings. This takes place by releasing or by enzymatic substrate conversion on the particle surface. There is no measurable signal here, which depends on the substrate concentration, as for example for other biosensors. Indeed, the measurable signal is determined by the number of marker particles located close to the microelectrode.

Figure 23:
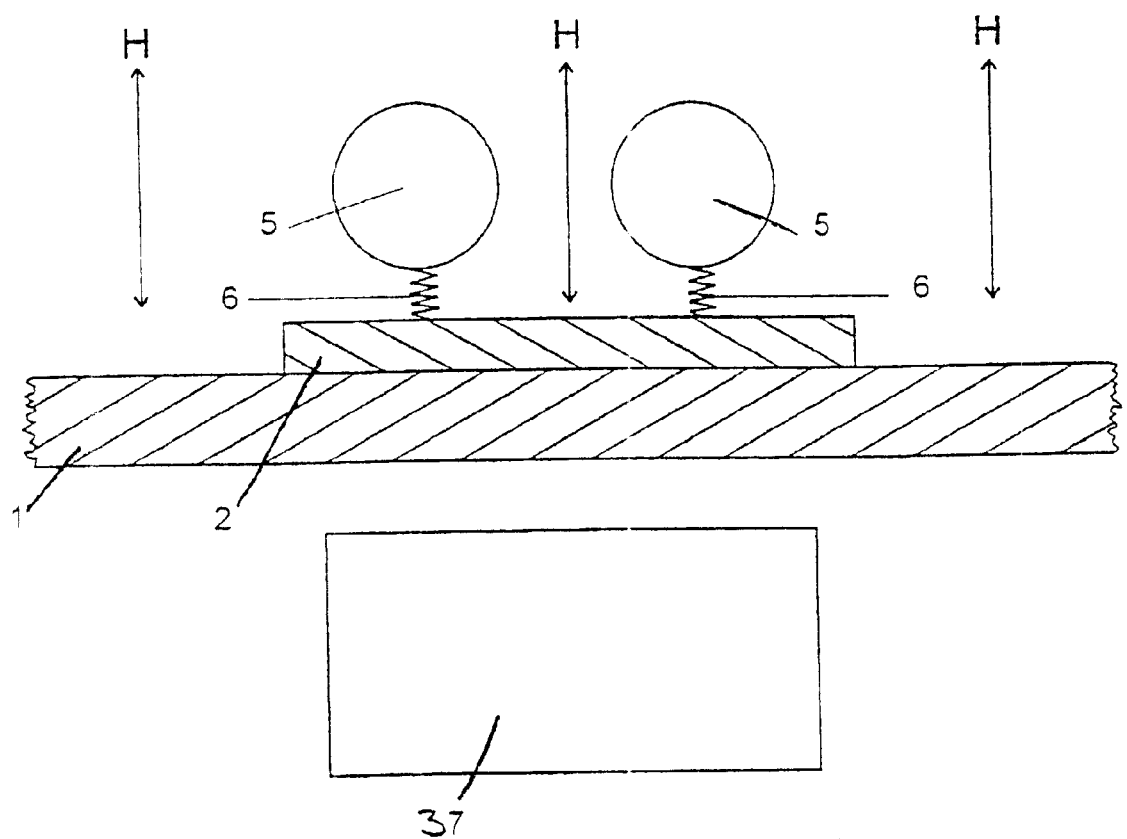
FIG. 23 shows schematically a representation of the bond in the magnetic alternating field.

FIG. 23 shows a further exemplary embodiment. A microelectrode 2 is attached to a support 1. If there is binding 6 between marker particles 5 and the electrode 2, as described above, the marker particles are located close to the microelectrode. If the marker particles are ferromagnetic with a separate magnetic field, location of the marker particles 5 close to the electrode nay be detected with the aid of a sensor 37, which measures the strength of the magnetic field.

Likewise, it is possible to use marker particles with paramagnetic core. If a magnetic alternating field 4 is now produced above the support 1, the change in the magnetic field strength caused by the marker particles may be detected with the aid of sensor 37. The frequency of the magnetic alternating field may lie between a few Hertz and a few MHz.

When using marker particles with ferromagnetic or paramagnetic core, it is important that the relative permeability of the particle or the particle core is different from the relative permeability of the liquid measuring medium, the substrate, and for through-flow measurement, the through-flow measuring chamber according to FIG. 4.

In this exemplary embodiment, the electrophoretic transport of binding molecular partners may take place towards the electrode 2. as has been described in the preceding exemplary embodiments. Likewise, it is possible to effect the transport of marker particles by electrophoretic effect.

FIGS. 24 to 30 show a measuring arrangement for detection of marker particles in measuring solutions, which show at least one electrode with a diaphragm arranged in front of it, whereas FIGS. 31 to 35 show a measuring arrangement for detecting marker particles in measuring solutions using potentiometric electrodes.

The above statements also apply to these exemplary embodiments, wherein the microelectrodes may be replaced by the electrodes described below.

FIG. 24a) shows a macroelectrode 2, which is situated in front of a diaphragm 101 made from electrically non-conducting material having a diaphragm opening 105. The space between the diaphragm 101 and the electrode 2 is filled with an internal electrolyte 103, which is in contact with the measuring medium 3 (electrolyte) via the diaphragm opening 105. The internal electrolyte may thus be designed, for example as a gel, wherein it is possible that it is extended into the diaphragm opening 105. A counter-electrode (not shown in the figure) is situated in the measuring medium at a considerable distance from the diaphragm 101. An electric direct and/or alternating voltage is applied to the electrodes, resulting in an electric field being produced between the electrodes. The electric field lines 4" emerging from the electrode 2 are concentrated in the region of the diaphragm opening 105. The electric field lines 4'" describe a radially expanding electric field in the measuring medium 3.

FIG. 24b) shows the electrode and diaphragm configuration with a label (marker) particle 5 which is bound to the diaphragm 101 with the aid of a bond 6, if the molecular binding partners are located in the vicinity of the diaphragm opening 105, binding of the label particle 5 takes place in the immediate vicinity of the diaphragm opening 105. The LIFE effect (Label Induced Field Effect) described above, that is a field effect induced by marker particles, leads to a disturbance in the electric field and the electric field lines 4'" in the measuring medium 3. This may be detected electrically, as described.

The size of the diaphragm opening 105 lies in the range between 0.5 $\mu$m and 100 $\mu$m, preferably in the range around 1 $\mu$m. The distance between the diaphragm 101 and the electrode 2 may be freely selected if it is considerably greater than the diameter of the diaphragm opening. This diaphragm distance is for example 1 mm. The diameter of the marker particles lies between 0.5 $\mu$m and 100 $\mu$m, preferably in the range around 1 $\mu$m.

Figure 24:
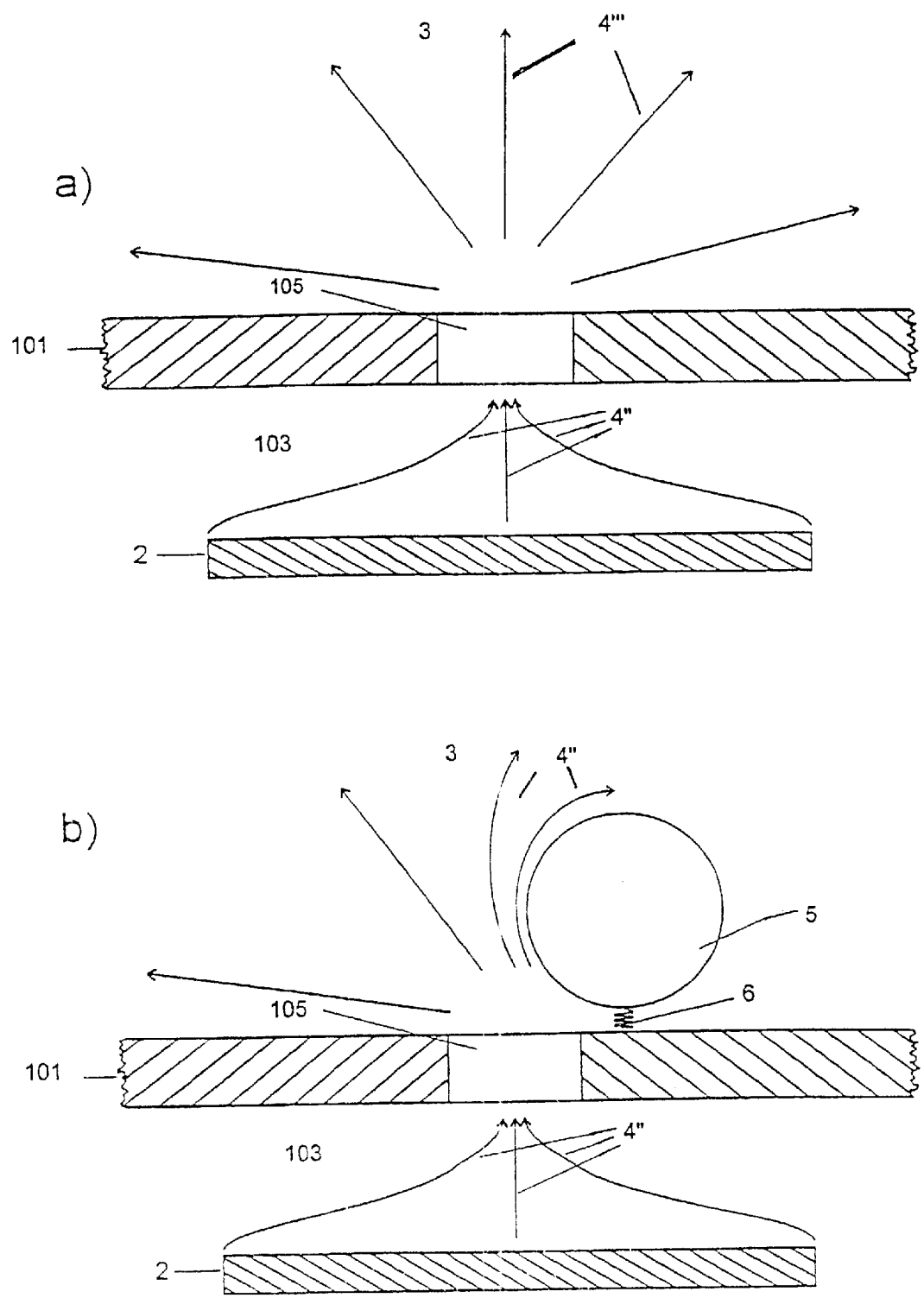
FIGS. 24*a*–*b* shows a schematic representation of an electrode and a diaphragm with electric flow lines without bound label particles and with a label particle bound in the vicinity of the diaphragm opening.
Figure 25:
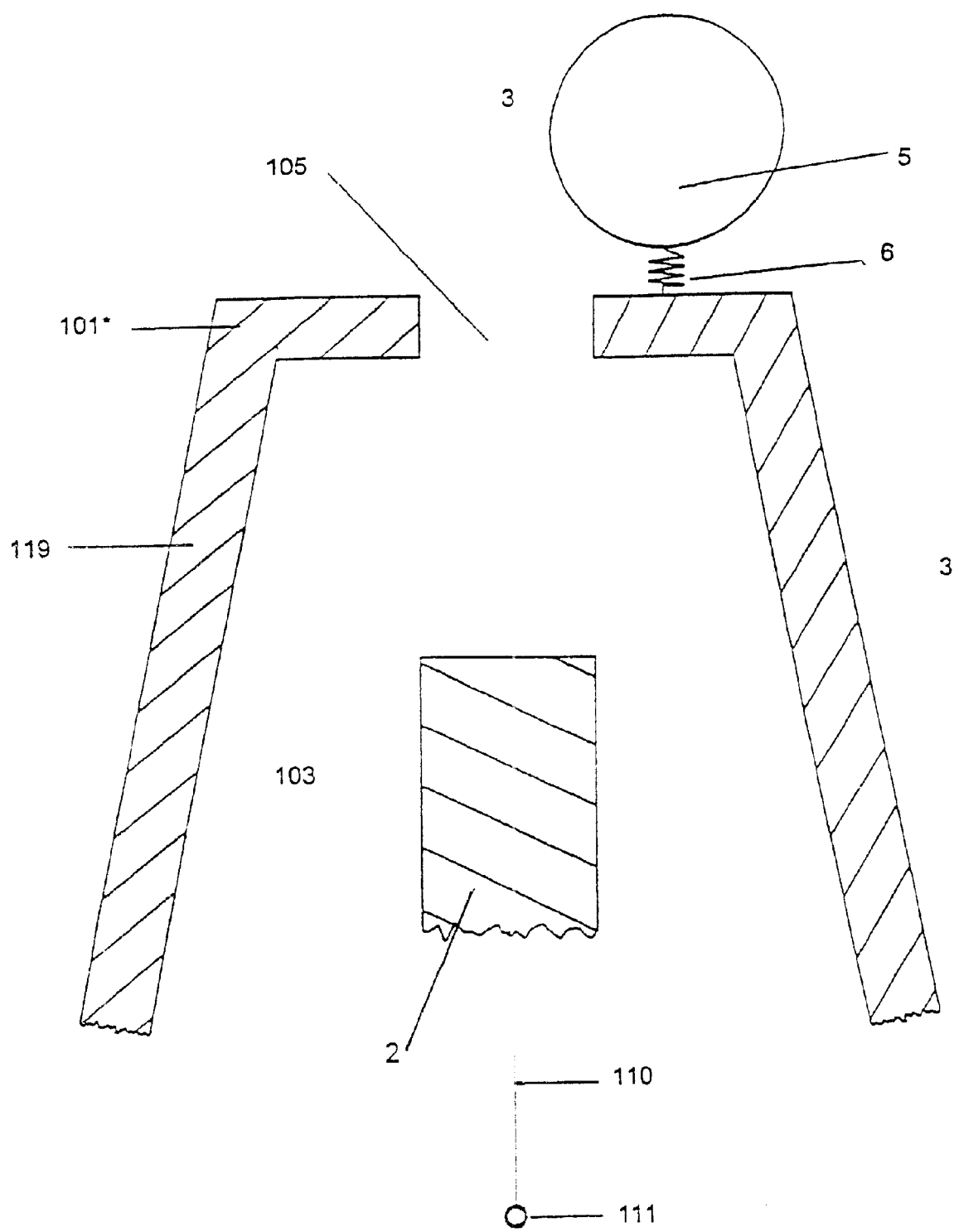
FIG. 25 shows a schematic representation of an electrode and diaphragm arrangement in pipette design, FIGS. 26*a*–*b* hows an electrode and diaphragm arrangement in planar layer structure.

FIG. 25 shows an electrode and diaphragm configuration in pipette technology. A micropipette 119, which consists for example of glass, has a diaphragm 101* with a diaphragm opening 105 at its tip. The pipette is filled with an internal electrolyte 103 into which an electrode 2 projects. The electrode 2 can be connected to measuring electronics with the aid of an electric lead 10 and an electric connection 111. Particles 5, which are located by bonds 6 in the vicinity of the diaphragm opening 105, lead, as shown in the example according to FIG. 24, to a disturbance in the electric field and thus can be detected electrically.

Figure 26:
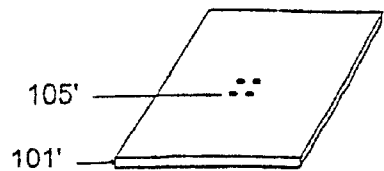
Figure 26:
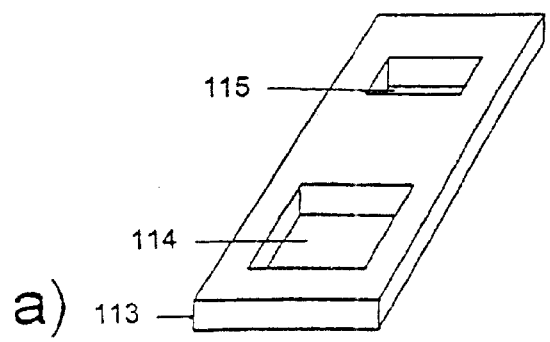
Figure 26:
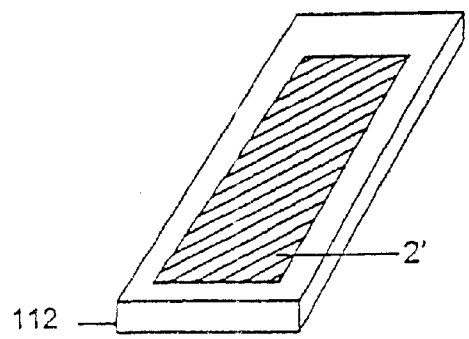
Figure 26:
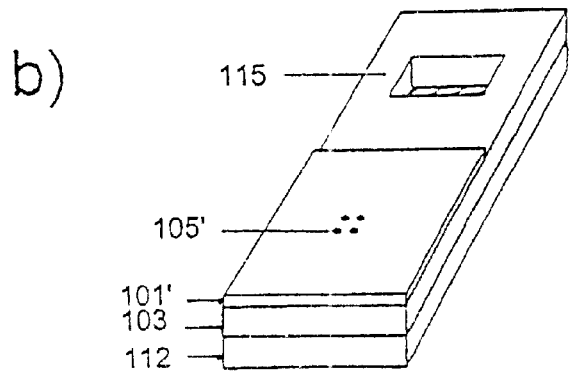

FIG. 26 shows an electrode and diaphragm configuration according to FIG. 24 in planar structure.

A thin electrode layer 2' is situated on a support 112. The support 112 may consist, for example of a plastic film. All materials having a high electrical resistance can be used for this. The electrode layer 2' may be applied, for example from a noble metal (gold, platinum, silver AgCl etc.) by known thin-layer processes. Likewise, it is possible to apply the electrode layer 2' with the aid of electrically conductive pastes by the screen printing process. A spacer 113 is applied to the support 112, for example by adhesive technology or by hot-lamination. The spacer 113 has a perforation 115 for electrical contact of the thin electrode layer 2' as well as a compartment 114 for the internal electrolyte. The spacer may be produced from the same material as the support 112. A diaphragm film 101' is applied to the spacer 113 by adhesion and hot-lamination technology. The diaphragm film 101' has one or more diaphragm openings 105'.

Introduction of the internal electrolyte into its compartment 114 may be effected, for example by the process of vacuum filling. The configuration according to FIG. 26b) is introduced into an electrolyte for this and a vacuum is produced above the electrolyte. Air is thus removed from the compartment 14 and the internal electrolyte moves in.

The diaphragm openings 105' on the diaphragm film 101' may be produced, for example with the aid of a laser. It is also possible to produce a perforated diaphragm film by the known LIGA process. Likewise, it is possible to realise the diaphragm film 101' in the form of an ion-track filter. Microscopic openings in the $\mu$m range and in the sub-$\mu$m range are produced in such ion-track filters. Furthermore, capillary pore membrane filters can be used which have pores in the $\mu$m and in the sub-$\mu$m range. Such capillary pore membrane filters are commercially available and consist, for example of the materials polycarbonate, polyester, acrylic polymer, PP.

It is important when using more Than one diaphragm opening 105, that for a diaphragm opening diameter of 0.5 $\mu$m–10 $\mu$m distances are maintained from diaphragm openings which are about 100 $\mu$m. This guarantees that the electric field lines extend radially into the measuring medium starting from the diaphragm openings 105.

Figure 27:
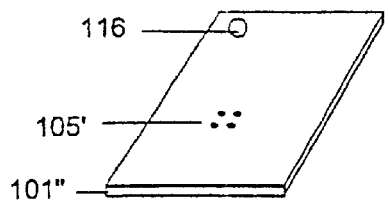
FIGS. 27*a*–*b* shows an electrode and diaphragm arrangement in planar layer structure according to a further embodiment.
Figure 27:
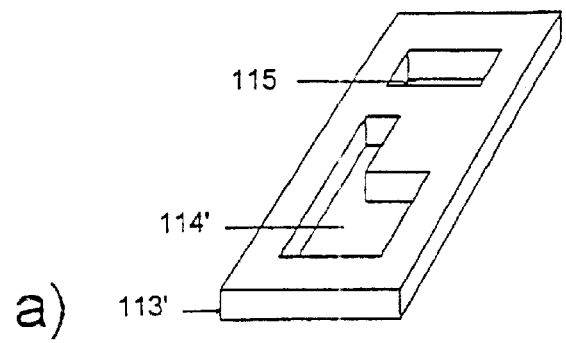
Figure 27:
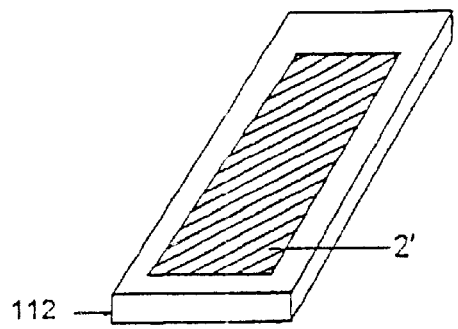
Figure 27:
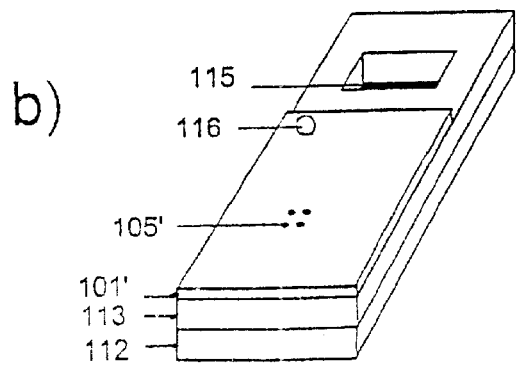

FIG. 27 shows a first variant to the configuration in FIG. 26. Here the spacer 113' is equipped with a compartment 114' for the internal electrolyte, which offers an additional facility for removing air from this compartment. An opening 116, by means of which the air may be removed from the sample compartment more rapidly when filling by vacuum, is situated in the diaphragm film 101". After filling the configuration according to FIG. 27, the air-removal opening 116 may be sealed using a suitable material (epoxy resin, silicone, etc.). Otherwise, the structure corresponds to that according to FIG. 26.

Figure 28:
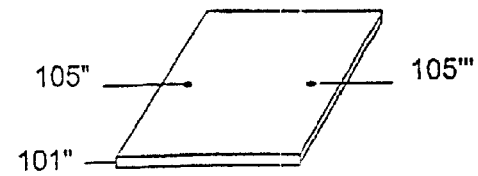
FIGS. 28a–b shows an electrode and diaphragm arrangement in planar layer structure with two electrodes and corresponding diaphragms.
Figure 28:
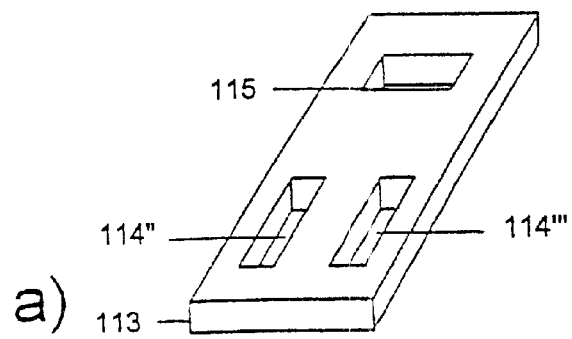
Figure 28:
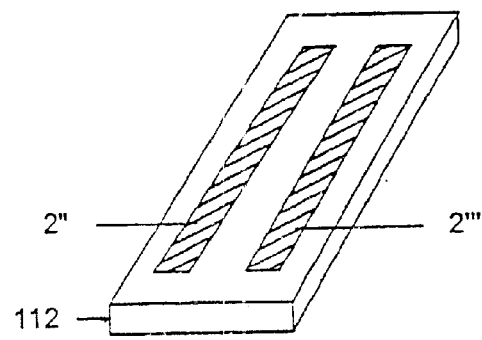
Figure 28:
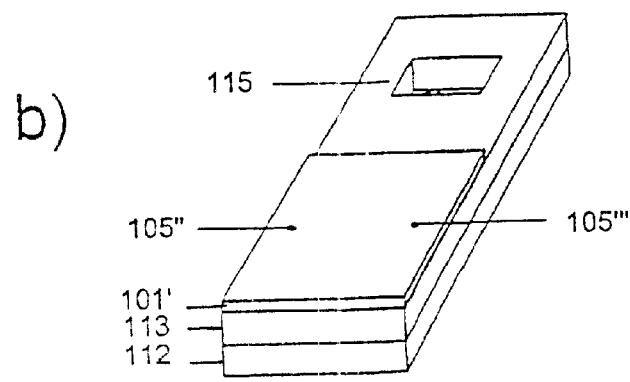

FIG. 28 shows a second variant of the configuration according to FIG. 3. Two electrode layers 2", 2'" are situated on the support 112 here. In this embodiment the diaphragm film 101" supports two diaphragm openings 105", 105'". If different molecular binding partners are immobilised in the immediate surroundings of the diaphragm openings 105" and 105'", different analytes can be detected. This corresponds to an arrangement of two microelectrodes, as described above. The configuration with two electrodes and associated diaphragm openings may also be expanded to a larger array with a plurality of electrode and diaphragm openings.

Figure 29:
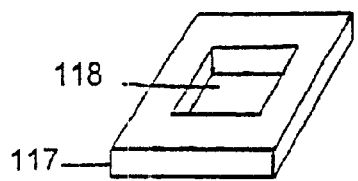
FIGS. 29a–b shows an electrode and diaphragm arrangement in planar layer structure with a counter-electrode.
Figure 29:
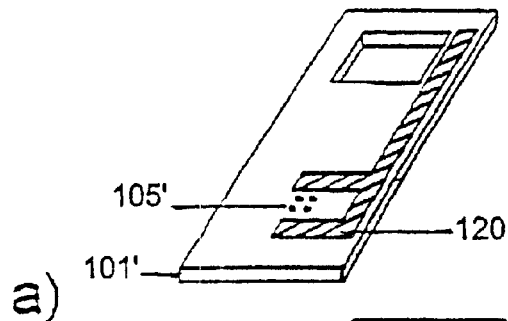
Figure 29:
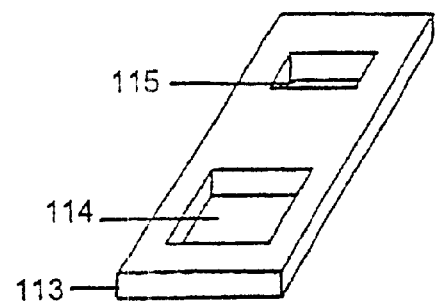
Figure 29:
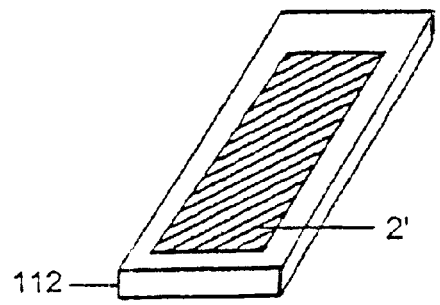
Figure 29:
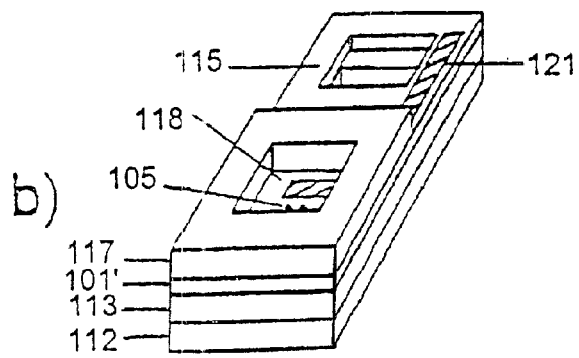

FIG. 29 shows a further variant of the configuration according to FIG. 26. Here a support 117 for a sample compartment 118 is additionally applied to the diaphragm film 101'. This support 117 may be produced from any plastic which is compatible with the sample used, and can be applied to the diaphragm film 101' by adhesion technology or by hot-lamination and by a different process. In addition, a counter-electrode 120 is applied to the diaphragm film 101' here. The same applies to the application and the material of the counter-electrode as is described for the electrode 2 in the example according to FIG. 26. The counter-electrode 120 may be contacted at the electrical connection 121. Devices with sample compartments may also be realised in array form with a plurality of compartments.

Figure 30:
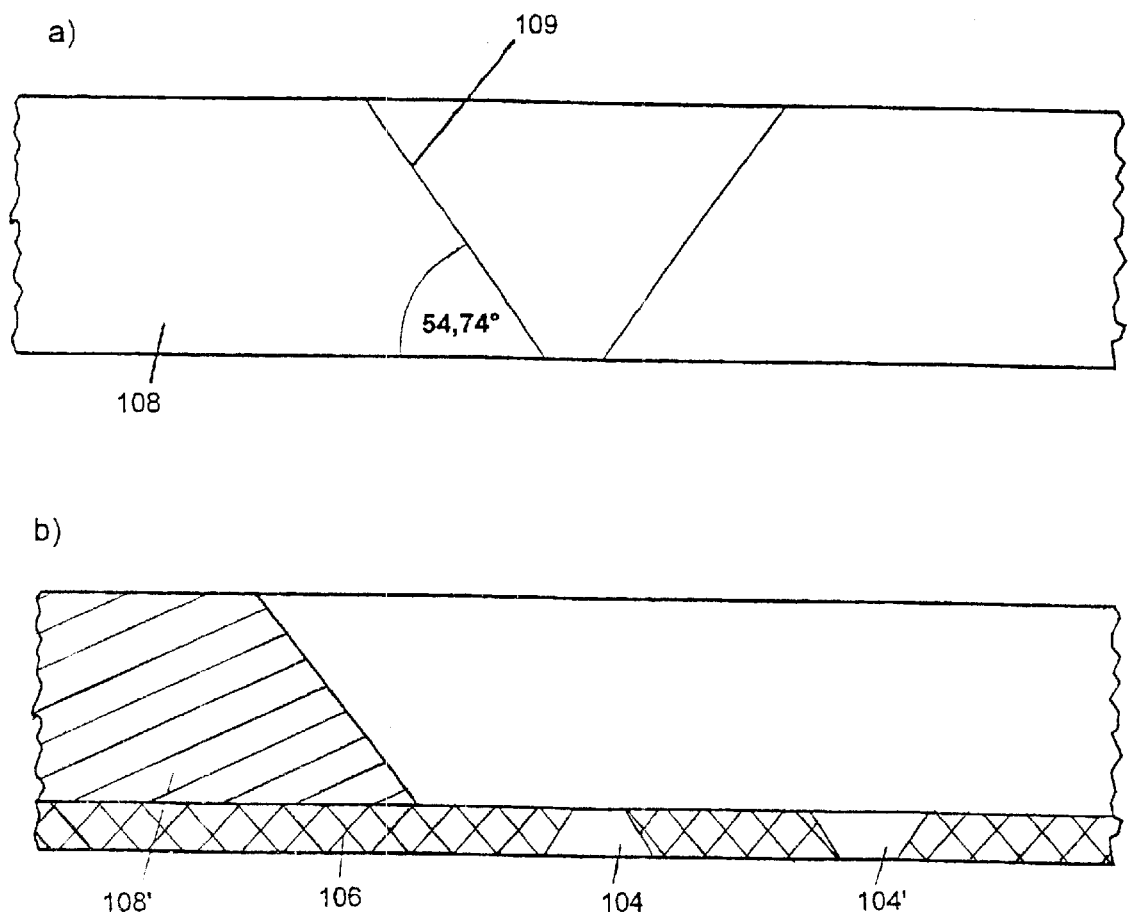
FIGS. 30a–b shows a further embodiment of a diaphragm

FIG. 30 shows a particular embodiment of the diaphragm 101, as shown in FIG. 24 and below.

In this novel exemplary embodiment, the diaphragm is realised based on a silicon disc. A silicon disc 108 was perforated with the aid of known anisotropic etching processes. Openings 109 which have a pyramid-stump shape character are thus produced. It is also possible in this manner to realise very small openings. If, for example the opening on the lower side of the silicon disc 108 is to be about 1 $\mu$m, the large opening on the front side of the silicon disc is about 8 $\mu$m. The silicon disc is insulated electrically on the surface after introducing the openings 109. This can be realised, for example by thermal oxidation and/or by CVD processes using $Si_3N_4$.

FIG. 30b shows a variant of the diaphragm according to FIG. 30a. A layer 106 was deposited on a support 108' by known epitaxic processes. The silicon disc 108' can be etched above the layer 106 by known anisotropic etching processes in site-selective manner. Openings 104 and 104' may be introduced into the layer 106 with the aid of lithographic processes. This example has the advantage that the openings are situated in a very thin layer 106. The silicon disc may have a thickness of about 300 $\mu$m, whereas the layer 106 has a thickness between 1 and 100 $\mu$m (preferably 10 $\mu$m).

Figure 31:
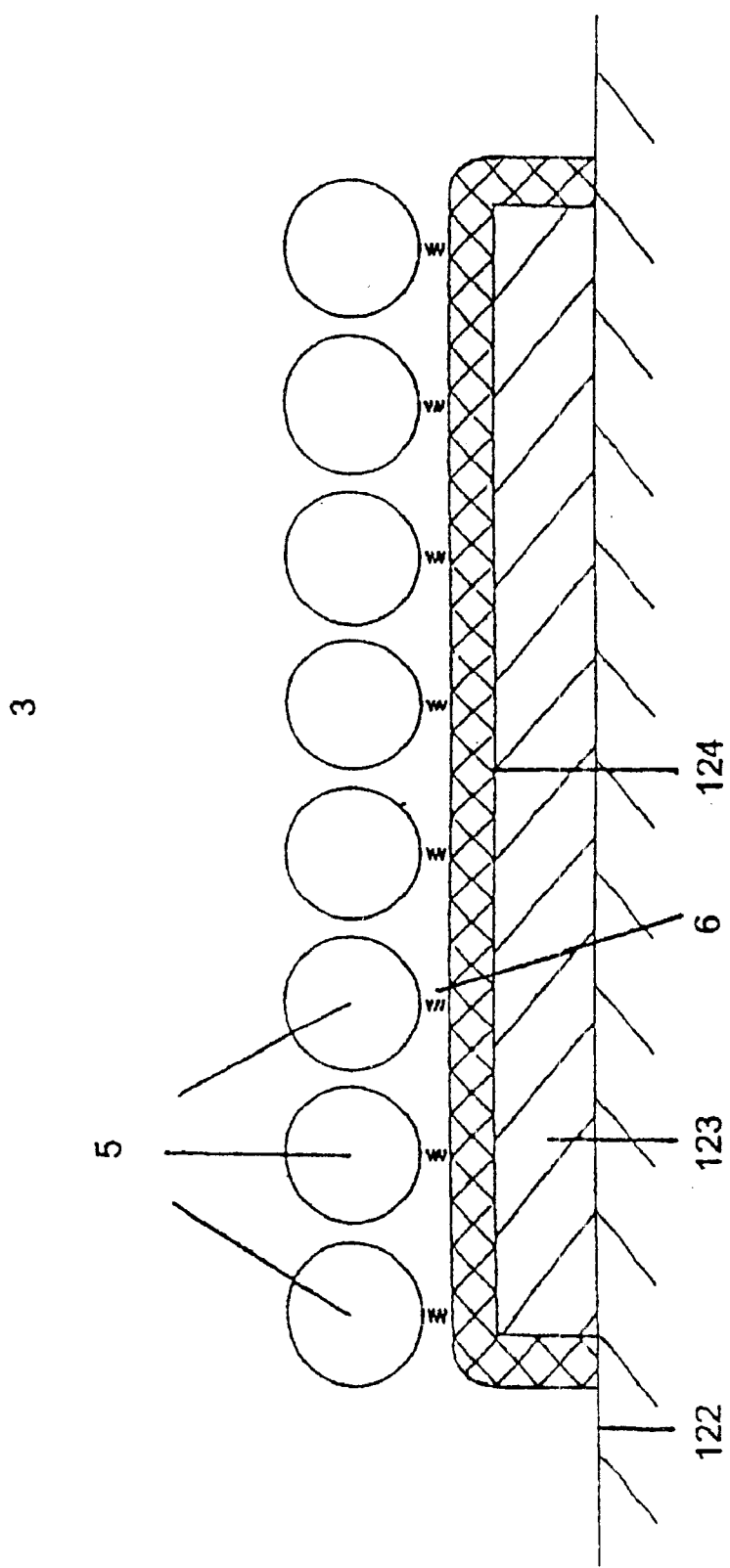
FIG. 31 shows a schematic representation of a potentiometric electrode with bound marker particles.

FIG. 31 shows a measuring arrangement for a process for potentiometric measurement for the detection of analytes.

The fixed leakage 123 of a potentiometric electrode with an ion-selective membrane 124 is situated on a support 122. Molecules which are able to enter binding 6 with the molecules which are immobilised on the particles 5, are immobilised on the surface of the ion-selective membrane 124. The label or marker particles 5 bound to the surface of the ion-selective membrane 124 and which have a diameter of 10 nm in this exemplary embodiment, cause a disturbance in the potential-forming steps at the surface of the ion-selective membrane 124, which may be measured by potentiometric means. The potential of the ion-selective electrode comprising fixed leakage 123 and ion-selective membrane 124 is measured against a reference electrode, which is likewise situated in the measuring medium 3, but is not shown.

In this exemplary embodiment, the support 122 is, for example made of glass, the fixed leakage 123 of the potentiometric electrode consists of silver and the ion-selective membrane 124 of an Ag/AgCl layer.

Likewise, it is possible to design the ion-selective membrane 124 as a polymer membrane. Other known materials for ion-selective membranes may also be used. It is also possible to arrange a further layer, in which the immobilised binding partners are situated, above the ion-selective membrane without immobilised molecules (without figure). This layer may consist, for example of a hydrogel or collagen.

Figure 32:
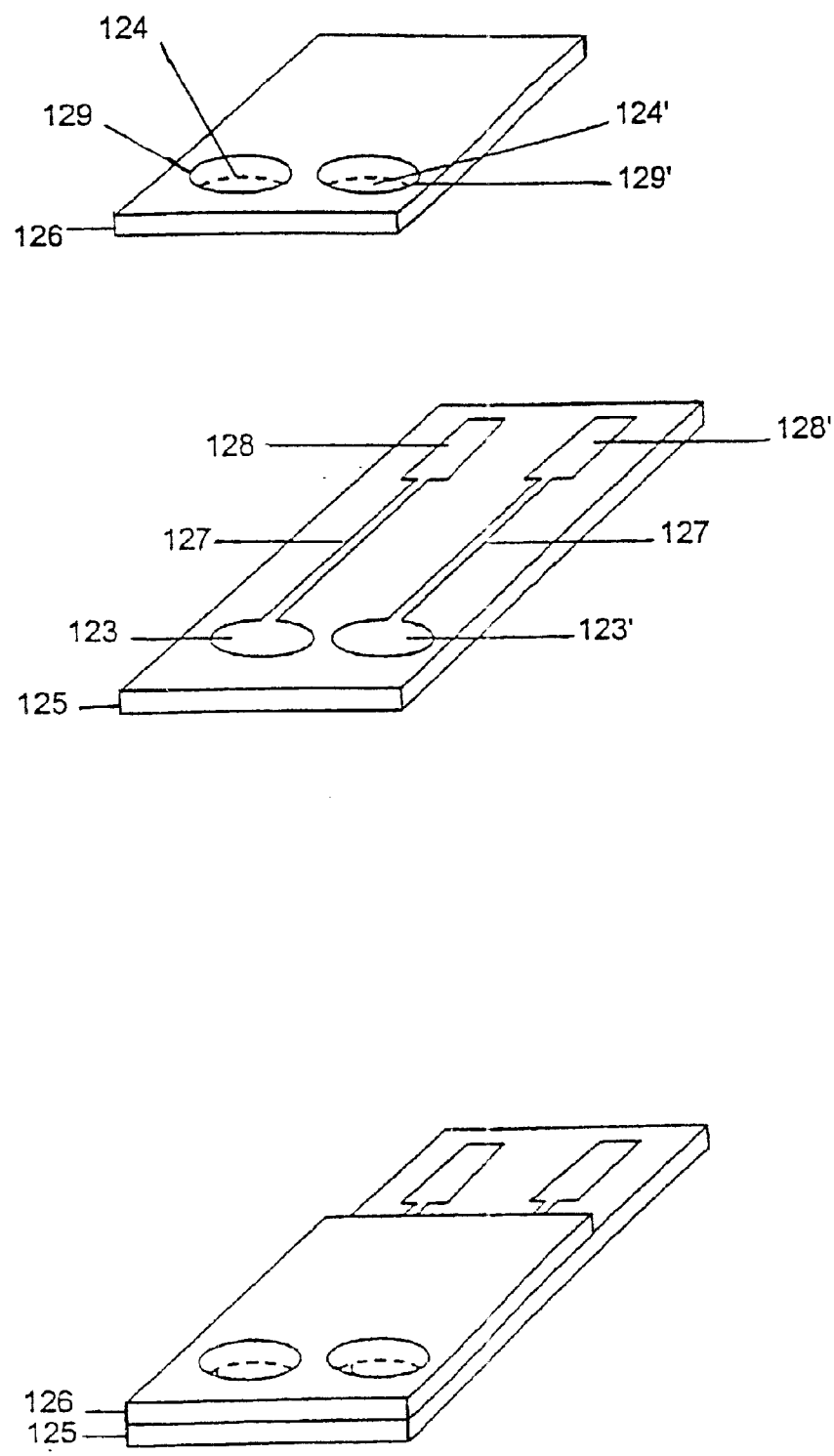
FIG. 32 shows a realisation of two potentiometric electrodes on a planar support for a differential measurement.

FIG. 32 shows an exemplary embodiment for the use according to the potentiometric measuring principle in the differential process. The fixed leakages 123 and 123' of a potentiometric electrode with the conductor strips 127 and 127' and the electrical connections 128 and 128' are situated on a support 125. Support and electrodes as well as conductor strips are protected with respect to the measuring medium by the covering 126. The covering 126 has perforations 129 and 129' which expose the ion-selective electrodes. The fixed leakage 123 and 123', the conductor strips 127 and 127' as well as the electrical connections 128 and 128' may be produced, for example from silver by known thin-layer or thick-layer processes. In turn, Ag/AgCl may be used as ion-selective membrane, wherein they may be produced by chloridisation of the silver film of the fixed leakages 123, 123'.

Likewise, it is possible to produce polymer membranes with electroactive components in the perforations 129 and 129' by known processes. Dispensing processes can be used for this. The covering 126 may be applied by screen printing processes. The introduction of the ion-selective membranes 124 and 124' may also be effected by screen printing processes.

If molecules, which may enter a bond 6, are immobilised on the surface of the ion-selective membrane 124, the signal of this electrode can be compared with the signal of an ion-selective electrode using the ion-selective membrane 124', on the surface of which molecules are not immobilised, in a differential process. The potentials of both electrodes may be measured against an external reference electrode. Conventional reference electrodes are suitable for this. Likewise, any metal electrode can be used as a pseudo-reference.

The use of a differential process has the advantage that non-specific bonds of molecules on the surface of the ion-selective membrane are not recorded in this measuring process.

Figure 33:
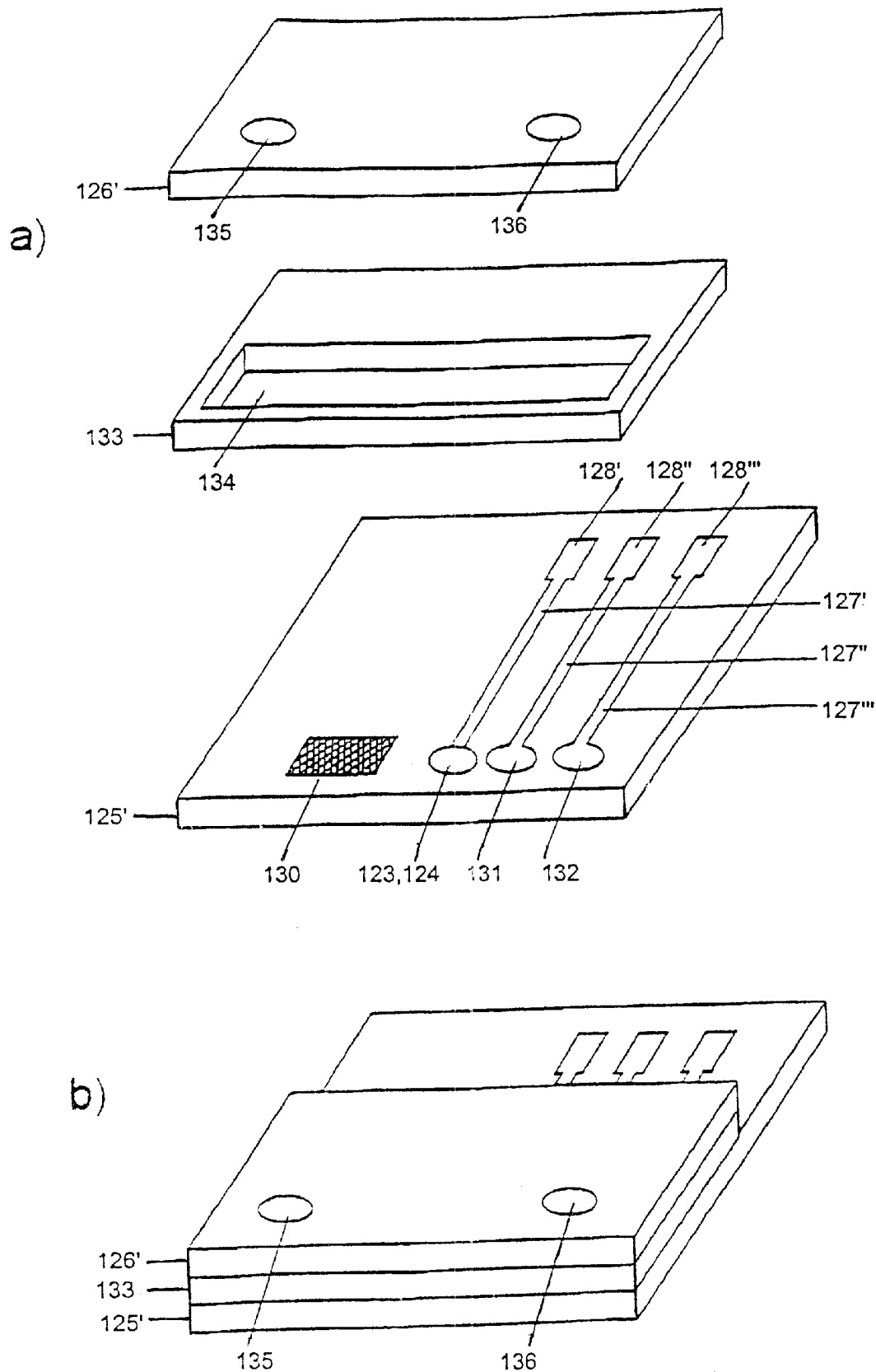
FIGS. 33a–b shows an electrode arrangement with integrated flow channel.

FIG. 33 shows in a further exemplary embodiment, a potentiometric electrode arrangement with integral flow channel. The fixed leakage 123 of a potentiometric electrode with an ion-selective membrane 124, which are connected to an electrical connection 128' via a conductor strip 127', are situated on a support 125'. A counter-electrode 131 and a reference electrode 132 are arranged adjacent thereto. The electrodes 131, 132 may consist of noble metal films, for example platinum. Marker particles, which may be released on contact with an aqueous measuring medium, are weakly immobilised on the support 125' on a surface 130. A channel support 133 is applied to the support 125' by adhesion technology or by hot-lamination. The channel support 133 has a perforation 134 which acts as a channel. The channel support 133 is closed with the aid of the covering 126'. The aqueous measuring medium may be supplied and discharged through the perforations 135, 136. The covering 126 is applied to the channel support by adhesion technology or hot-lamination.

Figure 34:
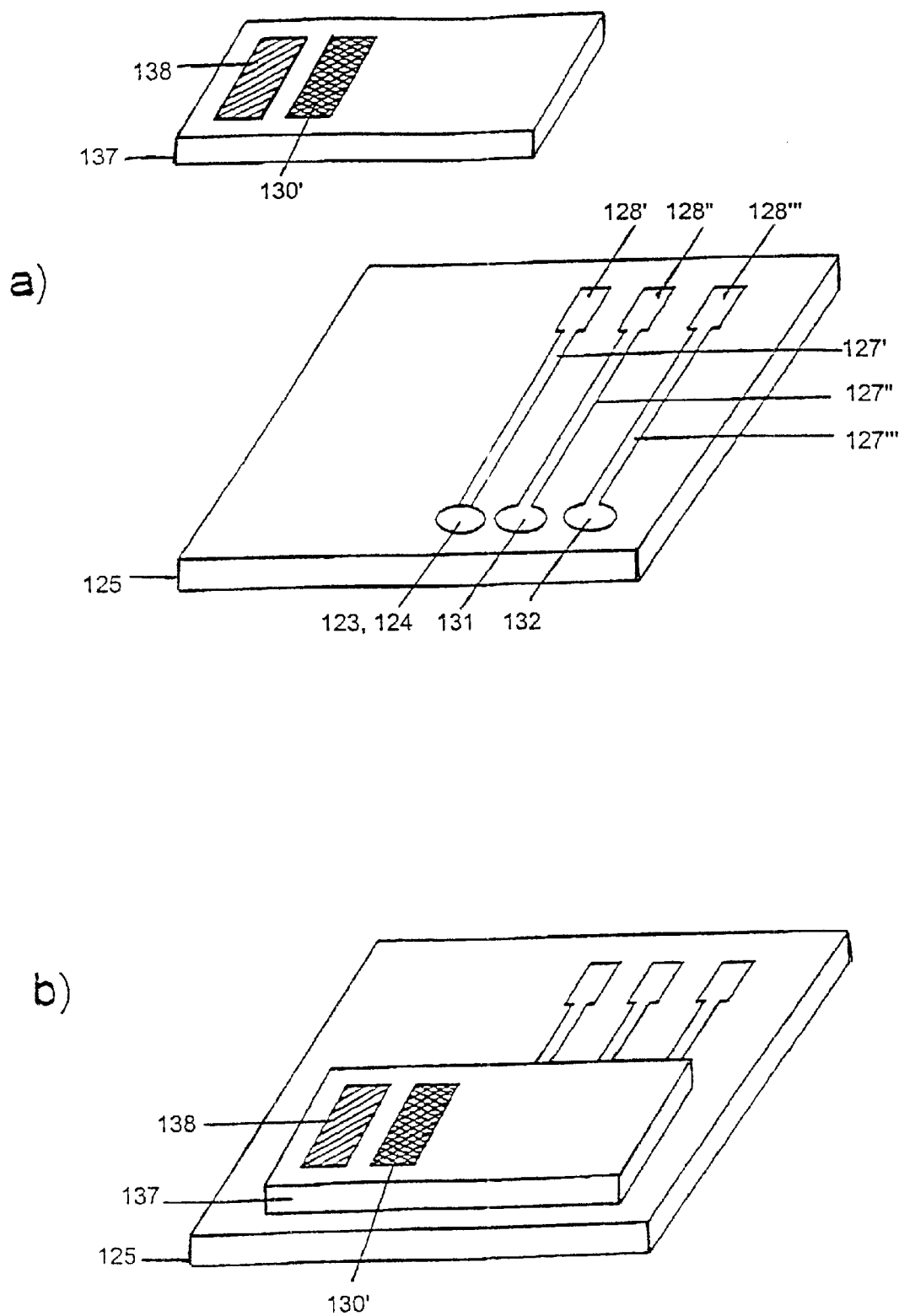
FIGS. 34a–b shows an electrode arrangement with integrated flow matrix.

In FIG. 34 the channel from FIG. 33 is realised as a flow matrix 137. The same electrode arrangement as in FIG. 33 is situated on a support 125. A flow matrix 137 is arranged above the electrodes. It consists, for example of filter paper or a glass fibre matrix or other materials which are applied by adhesion processes or by pressing onto the support 125. Marker particles are weakly immobilised on the surface 30'. The aqueous measuring medium is applied to the surface 138 which serves to receive a sample. If the measuring medium expands into the flow matrix 137, marker particles are released in the region of the surface 130' and transported to the electrodes 123, 124, 131 and 132.

Figure 35:
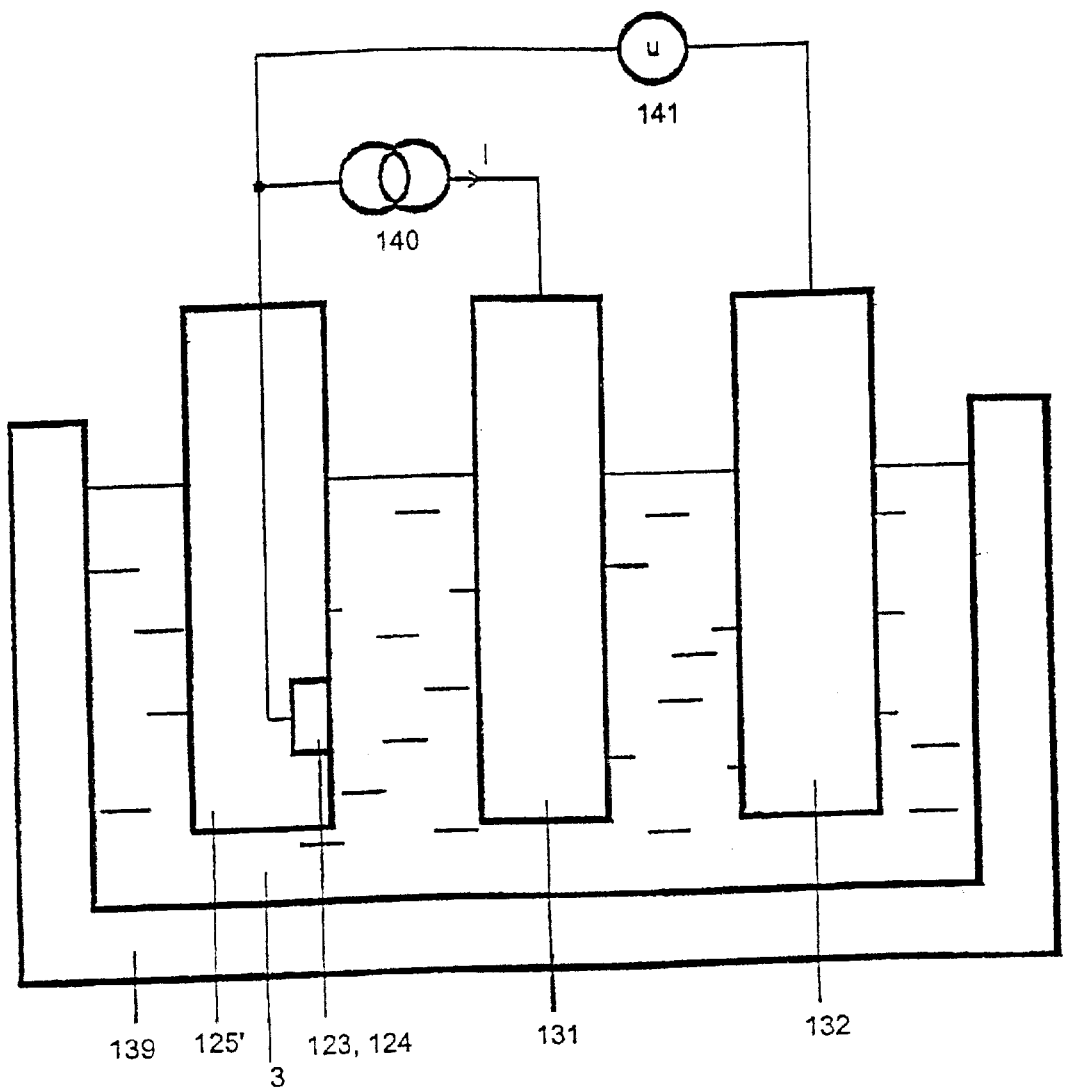
FIG. 35 shows an electrical circuit with a potentiometric electrode and counter- and reference electrodes.

The potentiometric measurement with the aid of devices according to FIGS. 33 and 34 may be effected with the aid of an electric circuit which is shown schematically in FIG. 35. The aqueous measuring medium 3 is situated in a sample container 139. A support 125' with an ion-selective electrode comprising fixed leakage 123 and ion-selective membrane 124, a counter-electrode 131 and a reference electrode 132 are immersed in the measuring medium 3. An electric current is supplied between the ion-selective electrode and the counter-electrode with the aid of a current source 140. The potentiometric measuring signal may be measured as electric voltage between the ion-selective electrode 123, 124 and the reference electrode 132 by potentiometric means using a high-resistance voltage measuring device 141.

Marker particle transport by electrophoretic means takes place with the aid of the electric current between the ion-selective electrode and the counter-electrode. This is possible when using potentiometric electrodes which have relatively low resistance. This is the case, for example for Ag/AgCl electrodes.

In high-resistance potentiometric electrodes, the counter-electrode 131 and the current source 140 are dispensed with. Marker particle transport must thus take place by magnetic means, as described further above.

The assays described can be used not only for the analytes described here, but also generally for detection of antibodies, antigens nucleic acids, aptamers or any other analytes for analysis and/or diagnostics in chemistry, foodstuff chemistry, biotechnology, environmental analysis, biochemistry or medicine.

What is claimed is:

1. A process for detection of analytes in a measuring solution comprising the steps of:
   providing marker particles for binding specifically to the analytes, the particles having electrical properties which are different from the measuring solution;
   arranging an electrode so that an electric field and an electric current are produced in the solution; and
   determining changes in the electric current caused by the marker particles, wherein the electrode arrangement produces an inhomogeneous electric field and the marker particles are electrically insulating.

2. Process according to claim 1, wherein at least two electrodes are used as the electrode arrangement, wherein at least one of the electrodes is a microelectrode and the surface area of the at least one microelectrode is approximately equal to the cross-sectional surface area of one of the marker particles, wherein the marker particles have a diameter less than about 10 $\mu$m.

3. Process according to claim 1, wherein the different electrical properties is dielectric constant.

4. Process according to claim 1, wherein the analytes specifically bound to marker particles bind in turn specifically to a substrate.

5. Process according to claim 1, wherein free analytes with marker particles or with marker particles to which the analytes are bound, compete around binding sites specific to the free analytes on a substrate which is the electrode used for producing an electric field.

6. Process according to claim 1, comprising providing a second electrode, wherein the measuring solution with marker particles which bind specifically to the analytes flows between the two electrodes, by means of which the electric field is produced.

7. Process according to claim 1, comprising producing a magnetic field which exerts a force on the marker particles before determining the change in electric current due to the marker particles.

8. Process according to claim 7, wherein an alternating voltage and/or a magnetic field alternating its direction is produced in the measuring solution.

9. Process according to claim 7, wherein the electric and/or magnetic field is designed such that it exerts a force in the direction of a substrate provided with binding sites for the marker particles, on the marker particles towards and/or away from the substrate.

10. Process according to claim 1, wherein at least two electrodes are used as the electrode arrangement, wherein a diaphragm with an opening for the passage of electric field is arranged in front of at least one of the electrodes, and the marker particles are bound on or in the vicinity of a surface of the diaphragm.

11. A device for determination of analytes in a measuring solution, comprising:

marker particles which specifically bind to the analytes and have electrical properties which are different from the measuring solution;

an electrode for producing an electric field and an electric current in the measuring solution; and a measuring device for recording the electric current, wherein an inhomogeneous electric field is produced by arrangement of the electrode and the marker particles are electrically insulating.

12. Device according to claim 11, comprising a second electrode for producing the electric field and the electric current resulting therefrom, wherein at least one of the electrodes is a microelectrode and the surface area of the at least one microelectrode is approximately equal to the cross-sectional surface area of one of the marker particles, wherein the marker particles have a diameter less than about 10 $\mu$m.

13. Device according to claim 11, comprising a support on which a substrate having specific binding sites of the analytes is arranged and wherein the marker particles have specific binding sites for the analytes or the substrate, wherein marker particles are arranged on the support or a covering.

14. Device according to claim 13, wherein the substrate is a microelectrode.

15. Device according to claim 11, comprising a second electrode for producing the electric field and the electric current resulting therefrom and wherein the first and second electrodes are components of a through-flow cell, wherein an opening for the passage of the measuring solution exists between the two electrodes.

16. Device according to claim 11, comprising a covering, which covering is sealed externally by a membrane containing a marker particle which is permeable to the analytes and to the measuring solution.

17. Device according to claim 11, wherein the inhomogeneous electric field has a magnetic element of reversible polarity.

18. Device according to claim 14, comprising a diaphragm which is connected to the measuring solution and which has one small opening and which serves as binding element for the marker particles, the diaphragm is arranged in front of the electrode for producing the electric field and the current resulting therefrom.

19. Device according to claim 18, wherein the space between the diaphragm and the electrode is filled with an electrolyte which is in contact with the measuring solution.

20. Device according to claim 19, comprising a flat support which supports the electrode, and a spacer element, wherein the spacer element is provided with at least one perforation to receive the electrolyte, and is connected to the flat support, and the perforation is covered by a covering serving as the diaphragm, in which at least one diaphragm opening is provided.

* * * * *